(12) United States Patent
Lehtinen et al.

(10) Patent No.: US 10,668,117 B2
(45) Date of Patent: Jun. 2, 2020

(54) IMMUNOMODULATORY COMPOSITION COMPRISING BIFIDOBACTERIA

(71) Applicant: DUPONT NUTRITION BIOSCIENCES APS, Copenhagen K (DK)

(72) Inventors: Markus Lehtinen, Vantaa (FI); Sampo Lahtinen, Lohja (FI); Ronald B. Turner, Charlottesville, VA (US)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 0 days.

(21) Appl. No.: 15/544,989

(22) PCT Filed: Jan. 27, 2016

(86) PCT No.: PCT/EP2016/051695
§ 371 (c)(1),
(2) Date: Jul. 20, 2017

(87) PCT Pub. No.: WO2016/120320
PCT Pub. Date: Aug. 4, 2016

(65) Prior Publication Data
US 2019/0099457 A1    Apr. 4, 2019

Related U.S. Application Data

(60) Provisional application No. 62/108,260, filed on Jan. 27, 2015.

(51) Int. Cl.
| | |
|---|---|
| *A61K 35/745* | (2015.01) |
| *A61P 11/00* | (2006.01) |
| *A23L 33/135* | (2016.01) |
| *A61P 31/12* | (2006.01) |
| *G01N 33/569* | (2006.01) |

(52) U.S. Cl.
CPC .......... *A61K 35/745* (2013.01); *A23L 33/135* (2016.08); *A61P 11/00* (2018.01); *A61P 31/12* (2018.01); *G01N 33/56983* (2013.01); *G01N 2333/52* (2013.01)

(58) Field of Classification Search
None
See application file for complete search history.

(56) References Cited

FOREIGN PATENT DOCUMENTS

| RU | 2146935 C1 | 3/2000 |
| WO | WO-2012/049301 A1 | 4/2012 |
| WO | WO-2012/168732 A1 | 12/2012 |

OTHER PUBLICATIONS

Douglas et al., "Asthma: Clinician's Desk Reference", pp. 21-29, Manson Publishing, 2010.
Ashraf et al., "Effect of cell-surface components and metabolites of lactic acid bacteria and probiotic organisms on cytokine production and induction of CD25 expression in human peripheral mononuclear cells", American Dairy Association, 2014, vol. 97, pp. 2542-2558.
Azad et al., "Probiotic supplementation during pregnancy or infancy for the prevention of asthma and wheeze: systematic review and meta-analysis", BMJ, 2013, pp. 1-15.
Barrangou et al., "Comparison of the Complete Genome Sequences of *Bifidobacterium animals* subsp. *lactis*", Journal of Bacteriology, 2009, vol. 191, No. 13, pp. 4144-4151.
Barlett et al., "Mouse models of rhinovirus-induced disease and exacerbation of allergic airway inflammation", Nature Publishing Group, 2008, vol. 14, No. 2, pp. 199-204.
Calder et al., "Conference on Transforming the nutrition landscape in Africa Plenary Session 1", Proceedings of the Nutrition Society, 2013, vol. 72, pp. 299-309.
Cheung, et al., "Rhinovirus Inhalation Causes Long-Lasting Excessive Airway Narrowing in Response to Methacholine in Asthmatic Subjects In Vivo", American Journal Respir Crit Care Med, 1995, vol. 152, pp. 1490-1496.
Contoli et al., "Role of deficient type III interferon-λ, production in asthma exacerbation" Nature Publishing Group, 2006, vol. 12, No. 9, pp. 1023-1023.
Contoli et al., "A human rhinovirus model of chronic obstructive pulmonary disease exacerbations", S. Karger AG, Basel, 2007, vol. 14, pp. 101-112.
Del Vecchio et al., "Utility of animal and in vivo experimental infection of humans with rhinoviruses in the development of therapeutic agents for viral exacerbations of asthma and chronic obstructive pulmonary disease", Pulmonary Pharmacology & Therapeutics, 2015, vol. 30, pp. 32-43.
Elazab et al., "Probiotic Administration in early life, atopy and asthma: A meta-analysis of Clinical trials", Pediatrics, 2013, vol. 132, No. 3, pp. e666-e-676.
FAO WHO Guidelines, "probiotics in food: health and nutrition properties and guidelines for evaluation", FAO Food and Nutrition Paper, World Health Organization, 2006, pp. 1-50.
Foligne et al., "Correlation between in vitro and in vivo immunomodulatory properties of lactic acid bacteria", World Journal of Gastroenterology, 2007, vol. 13, No. 2, pp. 236-243.
GB1503013.3 Search Report under Section 17(5).
Gunawardana et al., "Experimental Rhinovirus Infection in COPD: Implications for antiviral therapies", Antiviral Research, 2014, vol. 102, pp. 95-105.
Hao et al., "Probiotics for Preventing Acute Upper Respiratory Tract Infections", Cochrane Database of Systematic Reviews, 2011, Issue 9, pp. 1-46.
Heikkinen at al., "The Common Cold", The Lancet, 2003, vol. 361, pp. 51-59.

(Continued)

Primary Examiner — Padmavathi Baskar

(57) ABSTRACT

The present invention relates to composition derivable from a bifidobacteria, methods and uses thereof, for use in modulating the immune system in a subject by affecting viral action and/or viral effects in said subject. Furthermore, said composition may also be used in reducing the risk of development and exacerbation of chronic respiratory diseases such as asthma and COPD in a subject; preferably by modulating the immune system in the subject by affecting viral action and/or viral effects in said subject.

26 Claims, 11 Drawing Sheets
Specification includes a Sequence Listing.

(56) References Cited

OTHER PUBLICATIONS

Hojsak et al., "*Bifidobacterium animalis* subsp. *lactis* fails to prevent common infections in hospitalized children: a randomized, double-blind, placedbo-controlled study", The American Journal of Clinical Nutrition, 2015, vol. 101, pp. 680-684.
International Preliminary Report on Patentability, International Application No. PCT/EP2016/051695, international filing date, Jan. 27, 2016.
International Search Report, International Application No. PCT/EP2016/051695, international filing date, Jan. 27, 2016.
Jackson et al., "Evidence for a causal relationship between allergic sensitization and rhinovirus wheezing in early life", American J. Respir. Care Med, 2012, vol. 185, No. 3, pp. 281-285.
Kang, et al., "The Effects of Probiotics on Prevention of Common Cold: A Meta-Analysis of Randomized Controlled Trial Studies", Koren J. Fam Med, 2013, vol. 34, No. 1, pp. 2-10.
Kawahara et al., "Consecutive oral administration of *Bifidobacterium longum* MM-2 improves the defense system against influenza virus infection by enhancing natural killer cell activity in a murine model", Microbiol Immunol, 2015, vol. 59, pp. 1-12.
Mallia et al., "Neutrophil adhesion molecules in experimental rhinovirus infection in COPD", Respiratory Research, 2013, vol. 14, No. 72, pp. 1-9.
Maynard et al., "Reciprocal Interactions of the Intestinal Microbiotia and Immune System", Nature, 2012, vol. 489, No. 7415, pp. 231-241.
Message et al., "Rhinovirus-induced lower respiratory illness is increased in asthma and related to virus load and Th ½ cytokine and IL-10 production", PNAS, 2008, vol. 105, No. 36, pp. 13562-13567.
Mortaz et al., "Probiotics in the management of lung disease", Mediators of Inflammation, 2012, vol. 2013, Article ID 751068, 10 pages.
Proud, "Role of rhinovirus infections in asthma", Asian Pac J Allergy Immunol, 2011, vol. 29, pp. 201-208.
Sagar et al., "Bifidobacterium breve and Lactobacillus rhamnosus treatment is as effective as budesonide at reducing inflammation in a murine model for chronic asthma", Respiratory Research, 2014, vol. 56, No. 46. pp. 1-17.
Saglani, "Innate immunity in paediatric viral wheezers is virus specific and not interferon dependent", Thorax, 2014, vol. 69, No. 10, pp. 887-888.
Saraya et al., "Epidemiology of virus-induced asthma exacerbations: with special reference to the role of human rhinovirus", Review Article, 2014, vol. 5, Article 226, pp. 1-10.
Schneider et al., "Neonatal Rhinovirus Infection Induces Mucous Metaplasia and Airways Hyperresponsiveness", The Journal of Immunology, 2012, vol. 188, pp. 2894-2904.
Schwarze et al., "Respiratory Syncytial Virus Infection Results in Airway Hyperresponsiveness and Enhanced Airway Sensitization to Allergen", The American Society for Clinical Investigation Inc., 1997, vol. 100, No. 1, pp. 226-233.
Sigurs et al., "Asthma and allergy patterns over 18 years after severe RSV bronchiolitis in the first year of life", Thorax, 2010, vol. 65, pp. 1045-1052.
Stevenson et al., "Moving towards a new generation of animal models for asthma and COPD with improved clinical relevance", Pharmacology & Therapeutics, 2011, vol. 130, pp. 93-105.
Stevenson et al., "Comprehensive gene expression profiling of rat lung reveals distinct acute and chronic responses to cigarette smoke inhalation", Am J Physiol Lung Cell Mol Physiol, 2007, vol. 293, pp. 1183-1193.
Taipale et al., "*Bifidobacterium animalis* subsp. *lactis* BB-12 in reducing the risk of infections in infancy", British Journal of Nutrition, 2011, vol. 105, pp. 409-416.
Tate et al., "Critical Role of Airway Macrophages in Modulating Disease Severity during Influenza Virus Infection of Mice", Journal of Virology, 2010, vol. 84, No. 15, pp. 7569-7580.
Tourneur et al., "Neonatal Immune Adaptation f the Gut and Its Role during Infection", Clinical and Developmental Immunology, vol. 2013, Article ID 270301, 17 pages.
Vestbo et al., "Global Strategy for Diagnosis, Management, and Prevention of Chronic Obstructive Pulmonary Disease", Am J Respir Crit Care Med, 2013, vol. 187, No. 4, pp. 347-365.
Wall et al., "Role of Gut Microbiota in Early Infant Development", Clinical Medicine: Pediatrics, 2009, vol. 3, No. 45-54.
Wark et al., "Chlamydia pneumoniae immunoglobulin A reactivation and airway inflammation in acute asthma", European Respiratory Journal, 2002, vol. 20, pp. 834-840.
West et al., "Lactobacillus fermentum (PCC®) supplementation and gastrointestinal and respiratory-tract illness symptoms: a randomized control trial in athletes", Nutrition Journal, 2011, vol. 10, No. 30, pp. 1-11.
West et al., "Probiotic supplementation for respiratory and gastro-intestinal illness symptoms in healthy physically active individuals", Clinical Nutrition, 2014, vol. 33, pp. 581-587.
Written Opinion of the International Searching Authority, International Application No. PCT/EP2016/051695, International Filing Date Jan. 27, 2016.
Yawn "Factors accounting for asthma variability: Achieving optimal symptom control for individual patients", Primary Care Respiratory Journal, 2008, vol. 17, No. 3, pp. 138-147.

Study subject flow chart

Change in IL-8 concentration in nasal lavage over the course of the infection

Change in cytokine / chemokine response from day 0 (baseline) to day 4 (during infection)

The amount of rhinovirus in nasal lavage over the course of the infection

Percent of subjects (percent shedding) releasing rhinovirus to nasal lavage over the course of the infection

Phenotype of mice at day 56

A: Control Group

B: Probiotic Group

Quantification of the viral titer in the lung tissue

|  | D52 H2O | D52 Probiotics | D54 H2O | D54 Probiotics | D56 H2O | D56 Probiotics |
|---|---|---|---|---|---|---|
| Mean | 4610 | 3990 | 14398 | 11694 | 5906 | 4834 |
| Std. Error of Mean | 1050 | 1214 | 2674 | 966,3 | 1403 | 714,5 |

A: Total lymphocyte count in BALF

|  | D52 H2O | D52 Probiotics | D54 H2O | D54 Probiotics | D56 H2O | D56 Probiotics |
|---|---|---|---|---|---|---|
| Mean | 12100 | 3580 | 10640 | 16380 | 102120 | 108520 |
| Std. Error of Mean | 5855 | 1486 | 2325 | 2849 | 5952 | 23151 |

B: Proportion of lymphocytes in BALF

|  | D52 H2O | D52 Probiotics | D54 H2O | D54 Probiotics | D56 H2O | D56 Probiotics |
|---|---|---|---|---|---|---|
| Mean | 5,8 | 2,2 | 3,4 | 7 | 28 | 25 |
| Std. Error of Mean | 2,396 | 0,9695 | 0,8124 | 0,8944 | 1,517 | 4,159 |

A: Total macrophage count in BALF

| | D52 H2O | D52 Probiotics | D54 H2O | D54 Probiotics | D56 H2O | D56 Probiotics |
|---|---|---|---|---|---|---|
| Mean | 125920 | 137200 | 193200 | 138320 | 197800 | 264600 |
| Std. Error of Mean | 19229 | 24608 | 26097 | 29234 | 14616 | 22311 |

B: Proportion of macrophages in BALF

|  | D52 H2O | D52 Probiotics | D54 H2O | D54 Probiotics | D56 H2O | D56 Probiotics |
|---|---|---|---|---|---|---|
| Mean | 70 | 73,6 | 63 | 58,4 | 54 | 64,2 |
| Std. Error of Mean | 6,633 | 8,286 | 8,62 | 8,165 | 2,95 | 4,005 |

IMMUNOMODULATORY COMPOSITION COMPRISING BIFIDOBACTERIA

CROSS-REFERENCE TO RELATED PATENT APPLICATIONS

This patent claims priority under 35 USC § 371 as a national phase of Int'l Patent Appl. PCT/EP2016/051695 (filed Jan. 27, 2016; and published Aug. 4, 2016 as Int'l Publ. No. WO2016/120320), which, in turn, claims priority to U.S. Provisional Patent Appl. No. 62/108,260 (filed Jan. 27, 2015). The entire texts of the above-referenced patent applications are incorporated by reference into this patent.

FIELD OF INVENTION

The present invention relates to compositions derivable from a bifidobacteria, and methods and uses thereof, wherein said composition modulates the immune system. In particular, said compositions affect viral action and reduce viral effects. For example, alleviate inflammation caused by virus infection and inhibit of virus replication.

Furthermore, this invention reduces the risk of development, and reduces the severity and incidence of exacerbation of, chronic respiratory diseases such as asthma and chronic obstructive pulmonary disease (COPD).

REFERENCE TO SEQUENCE LISTING SUBMITTED ELECTRONICALLY

The official copy of the sequence listing is submitted electronically via EFS-Web as an ASCII formatted sequence listing with a file named NB40880USPCT_listing_ST25.txt created on Jun. 7, 2017 and having a size of 1 kilobyte and is filed concurrently with the specification. The sequence listing contained in this ASCII formatted document is part of the specification and is herein incorporated by reference in its entirety.

BACKGROUND

At birth a newborn infant is exposed to the microbiota of the mother, and microbes from the environment, which starts the colonization of mucosal surfaces in the digestive, respiratory and urogenital tracts, and the skin (Calder 2013). This process starts the maturation of the immune system. The colonizing microbiota and the intestinal immune system interact to establish life-time tolerance and mutualism between each other (Tourneur & Chassin 2013). This reciprocal interaction is a life-lasting process that influences the function and homeostasis of our immune system and well-being. Thus the composition and metabolism of the microbiota has direct influence on our immune health from birth to death (Maynard et al 2012). Therefore, modulation of the indigenous intestinal microbiota via the introduction of probiotic strains may play an important role in preventative health and in the management of specific conditions. (Wall et al 2009) The most generally accepted definition of probiotics was proposed by a FAO/WHO work group: "Live microorganisms which when administered in adequate amounts confer a health benefit on the host" (FAO/WHO. Guidelines for the evaluation of probiotics in food 2001. Food and Agriculture Organization of the United Nations (FAO). 2001.). The most commonly used probiotics are lactic acid bacteria, such as those belonging to the genera *Lactobacillus* and *Bifidobacterium*.

Pathogenic viruses have many forms and can cause many effects and symptoms. Furthermore, despite the commonness of viral infections, for most there is little treatment.

Human rhinovirus (HRV) infections are the cause of a common cold, and this disease places a large health and economic burden on society (Heikkinen T, Järvinen A. 2003).

Children have on average 6-8 colds annually and adults 1-4, of which approximately half are caused by the rhinoviruses (Heikkinen T, Järvinen A. 2003).

Usually, common cold itself is a self-limiting illness and will pass by without any medication. However, the symptoms are unpleasant and may last from several days to several weeks.

Rhinoviruses (and many other viruses) are typically caught from the environment by self-inoculation e.g. by touching one's nostril. HRVs then pass the nasal mucus and infect epithelial cells of the airways. The response of the epithelium and innate immune cells causes inflammatory response and secretion of inflammatory mediators such as cytokines and chemokines e.g. IL-1beta, IL-6, RANTES (CCL5), GM-CSF, IP-10, and of note IL-8. These cytokines mediate the attack of the immune cells against the virus infected cells that causes cold symptoms. In healthy subjects HRVs cause an inflammatory response and common cold symptoms that will pass by without any treatment. Similar immune responses occur in response to other virus infections.

HRV infections are associated with exacerbations of asthma, COPD, and idiopathic pulmonary fibrosis (IPF) in subjects suffering from these conditions (Saraya et al. 2014). In approximately 26-36% of asthma, 3-27% of COPD, and 5% of IPF cases HRV infections have been found to cause the exacerbations (Saraya et al. 2014; Table 1). Also other viruses like respiratory syncytial virus (RSV) and influenza are associated with the aetiology (Gunawardana et al. 2014 Antiviral Research). Furthermore, HRV infections together with RSV and metapneumovirus are associated with the early onset of wheezing episodes (bronchiolitis) in children (Saglani 2014). Approximately one-third of children who wheeze in the first 3 years of life continue to wheeze in later life and thus wheezing induced by viral infections or common cold is a risk factor for developing asthma (Sigurs et al. 2010; Jackson et al. 2012).

In asthmatics inflammatory cytokines, including IL-8, are known to worsen the pathology, and neutrophilic, lymphocytic and eosinophilic inflammation with airway hyperresponsiveness and airway remodeling characteristic to asthmatics are observed (Wark et al. 2002; Proud 2011). In asthmatics a deficient anti-viral mechanisms have been found (Contoli 2006) and it has been demonstrated that intranasally inoculated HRV induced clinical illness in asthmatics correlated to viral load and airway inflammation (Message et al. 2008).

There are several placebo-controlled clinical studies that have examined the efficacy of probiotics (Hao 2011; Kang 2014) in relation to common respiratory tract illness symptoms. These studies indicate that probiotic supplementation may reduce the incidence, and duration of illness in comparison to placebo supplements (Hao 2011 Kang 2014). However, these studies have only studied the symptoms of respiratory illness, not the causative agents, like viruses.

Clinical trials have looked at the efficacy of probiotics against the development of childhood asthma, but none of the studies have looked at the association of rhinoviruses with the asthma development (Azad 2013; Elazab 2013).

In COPD subjects, studies have found a role for inflammatory mediators in exacerbations and a clear association with viral infections exists (Gunawardana et al. 2014). A research team tested patients with mild COPD in an experimental rhinovirus model where HRV was inoculated to many of the noses of the volunteers; viral titers and inflammation were followed (Mallia et al. 2013). They demonstrated that IL-8 levels were higher in COPD patients than in healthy controls. Furthermore in nasal lavage of the COPD patients virus titer was found higher than in healthy controls (Gunawardana et al. 2014) that indicate deficient anti-viral defense mechanisms in COPD patients. Thus inflammation (indicated by IL-8) and viral titers are higher in COPD patients.

The inventors have surprisingly found that use of bifidobacteria modulates the immune system to not only affect viral action, but also reduce viral effects such as inflammation. Furthermore, in having this action the compositions of the current invention help in alleviating asthma and COPD exacerbations, and also reduce the risk of virus infection, such as HRV infection, that predisposes the subject to development of asthma or COPD in susceptible individuals.

SUMMARY

The present invention is based on the inventors surprising finding that use of a bifidobacteria (i.e. a *Bifidobacterium* spp.) modulates the immune system. In particular, these probiotics affect viral action and viral effects including virus replication, and/or alleviate inflammation caused by the virus infection.

The inventors have discovered that administration of a bifidobacteria to a subject results in inhibition of virus replication and decreased inflammatory response The inventors have further discovered that administration of a bifidobacteria to a subject modulates the adaptive immune response during the virus infection. In particular this occurs in rhinovirus infection.

Therefore, in one aspect of the present invention there is provided composition derivable from a bifidobacteria for use in modulating the immune system in a subject by affecting viral action and/or viral effects in said subject.

In another aspect of the present invention there is provided a method of modulating the immune system in a subject by affecting viral action and/or viral effects in said subject comprising use of a composition to be administered to and/or ingested by said subject; and wherein said composition is derivable from a bifidobacteria.

In a further aspect there is provided the use of a composition derivable from a bifidobacteria in the manufacture of a composition for modulating the immune system in a subject by affecting viral action and/or viral effects in said subject.

Also herein is provided a composition derivable from a bifidobacteria for use in reducing the risk of development and exacerbation of chronic respiratory diseases in a subject; preferably by modulating the immune system in the subject by affecting viral action and/or viral effects in said subject.

Preferably said composition of the invention is a medicament, a food product or a dietary supplement.

In another aspect there is herein provided a composition derivable from a bifidobacteria for use in modulating the immune system in a subject, or a method or a use of said composition, wherein modulation of the immune system modulates biomarker levels in the subject, preferably reduces biomarker levels in the subject. Preferably said biomarkers are cytokines and/or chemokines. Most preferably said biomarkers are IL-8 and/or IL-1beta and/or MCP-1.

Preferably said composition, method or use modulates the innate immune system, the adaptive immune system or both.

In a further aspect of the present invention, there is presented a composition derivable from a bifidobacteria for use in reducing the risk of development and exacerbation of chronic respiratory diseases in a subject. Preferably risk of development and exacerbation of chronic respiratory diseases is reduced due to modulation of the immune system by affecting viral action and/or viral effects in said subject; preferably inhibiting virus replication and/or alleviation of inflammation caused by the virus infection.

Preferably the composition of the invention reduces the risk of development and exacerbation of asthma and/or COPD.

In particular herein is provided a composition which reduces the risk of development and exacerbation of childhood asthma.

In one example used herein, said composition is derivable from a bifidobacteria, preferably a *Bifidobacterium* spp. preferably *Bifidobacterium animalis*, more preferably from *Bifidobacterium animalis* subsp. *lactis* (i.e. "*Bifidobacterium lactis*"), more preferably *Bifidobacterium lactis* BL-04.

Accordingly, preferably said composition is derivable from a bifidobacteria.

Accordingly, preferably said composition is derivable from *Bifidobacterium animalis*.

Accordingly, preferably said composition is derivable from *Bifidobacterium animalis* subsp. *lactis*.

Accordingly, preferably said composition is derivable from *Bifidobacterium lactis* BL-04—that is sometimes referred to as *Bifidobacterium lactis* subsp. *lactis* BL-04. The two terms are interchangeable.

For some embodiments, the bifidobacteria for use in accordance with the present invention has a good resistance to pepsin, under acid pH conditions, a good resistance to pancreatin and/or a good tolerance to the bile salts.

It will be understood that the composition according to the present invention may be formulated as a medicament, a food product or a dietary supplement. In a preferred embodiment, the composition is formulated as a dietary supplement.

Advantageously, where the product is a foodstuff, the bifidobacteria and/or a fermentation product of bifidobacteria and/or a cell lysate of bifidobacteria remain effective (e.g. the bacteria remain viable) through the normal "sell-by" or "expiration" date during which the food product is offered for sale by the retailer. Preferably, the effective time should extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

DETAILED DESCRIPTION

The detailed aspects of this invention are set out below. In part some of the detailed aspects are discussed in separate sections. This is for ease of reference and is in no way limiting. All of the embodiments described below are equally applicable to all aspects of the present invention unless the context specifically dictates otherwise.

In the following text, the term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where appropriate or necessary, the word "substantially" may be omitted from the definition of the invention.

The term "about" in relation to a numerical value z is optional and means, for example, z±20%, preferably z±15%, preferably z±10%, preferably z±5%.

The term "a" includes the singular as well as the plural.

The present invention provides in one embodiment a composition derivable from a bifidobacteria for use in modulating the immune system in a subject by affecting viral action and/or viral effects in said subject.

As used herein, the term "virus" has its normal meaning in the art, and therefore generally refers to a disease agent consisting only of genetic material, a protein coat and optionally a lipid envelope surrounding said protein coat.

Examples of viruses include rhinovirus, coronavirus, parainfluenza virus, adenovirus, enterovirus, or respiratory syncytial virus.

As used herein, the term "rhinovirus" refers to the causal agent of the common cold. This term encompasses any strain of the rhinovirus species in the genus Enterovirus of the Picornaviridae family of viruses. This term includes rhinoviruses A, B and C. "Human rhinovirus" is also referred to herein as "HRV".

As used herein, the term "virus infection" refers to the state wherein virus is present and multiplying in a subject. A virus infection may cause symptoms and illness in a subject, or may present as a subclinical infection without causing symptoms and illness in a subject.

Symptoms of rhinovirus infection include throat soreness, sneezing, blocked nose, fever, runny nose, a cough, coughing with chest congestion and coughing with wheezing.

Furthermore, rhinovirus infection may cause respiratory inflammation.

Said inflammation may be present in the lower respiratory tract or upper respiratory tract.

As used herein, the term "inflammation", encompasses any inflammation associated with virus infection, including for example tonsillitis, otitis media rhinitis (inflammation of the nasal mucosa); rhinosinusitis or sinusitis (inflammation of the nares and paranasal sinuses, including frontal, ethmoid, maxillary, and sphenoid); nasopharyngitis, rhinopharyngitis (inflammation of the nares, pharynx, hypopharynx, uvula, and tonsils); pharyngitis (inflammation of the pharynx, hypopharynx, uvula, and tonsils); epiglottitis or supraglottitis (inflammation of the superior portion of the larynx and upraglottic area); laryngitis (inflammation of the larynx); laryngotracheitis (inflammation of the larynx, trachea, and subglottic area); tracheitis (inflammation of the trachea and subglottic area); bronchitis (inflammation of the bronchi), bronchiolitis, acute bronchitis, and viral or bacterial pneumonia.

As used herein, the terms "viral effects" and "virus effects" are used interchangeably and refer to any one or more of the symptoms that a subject suffering from viral infection may experience, and in particular those discussed above such as throat soreness, sneezing, blocked nose, fever, runny nose, a cough, coughing with chest congestion and coughing with wheezing, tiredness, or any inflammation.

As used herein, the terms "illness" and "disease" refer to any deviation from or interruption of the normal structure and/or function of any body part, organ, or system that is manifested by a characteristic set of symptoms and signs. The term encompasses conditions with known or unknown etiology and/or pathology.

As used herein the term "respiratory tract illness" or "respiratory tract infection" refers to any illness affecting the respiratory tract, including both illnesses of the upper and lower respiratory tracts.

In one embodiment the respiratory tract illness is an upper respiratory tract illness. A respiratory tract illness may be caused by virus infection, such as rhinovirus infection, and may induce any one or more of the symptoms of virus infection or viral effects described above.

A respiratory tract illness may be temporary/acute or chronic and/or re-occurring.

A respiratory tract illness may result from environmental, allergenic or genetic factors, including bacterial or viral infection, or any combination of such factors.

In one embodiment the composition according to the present invention can be used for the treatment or prophylaxis of viral effects. In a preferred embodiment, the composition according to the present invention can be used for the treatment or prophylaxis of inflammation caused by the virus infection, in particular rhinovirus infection. In one embodiment the respiratory tract illness is a lower respiratory tract illness.

As used herein, the terms "viral action" or "virus action" are used interchangeably and mean any activity the virus itself conducts, such as infecting a subject or replicating.

In one embodiment the present invention relates to reducing one or more of the incidences, and/or duration or severity, preferably the incidence of, virus infection. In particular this occurs in COPD and/or asthma patients. Most preferably, the virus infection is rhinovirus infection.

In one embodiment the present invention relates to reducing one or more of the incidences, and/or duration or severity of, virus infection in subjects susceptible to asthma, in particular when such subjects are children. Most preferably, the virus infection is rhinovirus infection.

In another embodiment the present invention relates to reducing the incidence, duration or severity (preferably the incidence) of the viral effects experienced by a subject. In particular, reducing respiratory inflammation caused by the virus infection.

Preferably the reduction in the incidence (number or frequency), duration or severity of virus infection or alleviation of the viral inflammation caused by the virus infection is following administration of a composition derived from a bifidobacteria compared with the incidence (number or frequency), duration or severity, respectively, of virus infection or of the symptoms of virus infection in comparative subjects without administration of a composition derived from a bifidobacteria.

As used herein, the term "derivable" means obtained or produced from a source. The term "derivable" includes the term "derived". The compositions of the present invention are derivable from whole bifidobacteria, and/or fermentation products of bifidobacteria and/or cell lysate of bifidobacteria.

Chronic Respiratory Diseases

In one aspect of the present invention there is provided a composition derivable from for use in reducing the risk of development and exacerbation of chronic respiratory diseases, particularly asthma and COPD, in a subject.

In a preferred embodiment, the subject is a human subject. In a most preferred embodiment the subject is a human child, most preferably under 16 years of age. For some embodiments, the human child is under 10 years of age. For some embodiments, the human child is under 8 years of age. For some embodiments, the human child is under 6 years of age. For some embodiments, the human child is under 4 years of age. For some embodiments, the human child is about 3 years or less of age.

Furthermore, the current invention provides a method of reducing the risk of development and exacerbation of chronic respiratory diseases in a subject, said method comprising administering to said subject a composition derivable from a bifidobacteria.

In a further embodiment, the current invention provides the use of a composition derivable from a bifidobacteria in the manufacture or a composition for reducing the risk of development and exacerbation of chronic respiratory diseases in a subject.

The term "chronic respiratory disease" refers to respiratory tract illnesses, and any other disease of the respiratory system, including lung diseases, which persist constantly or reoccur throughout the life of a subject.

Chronic respiratory diseases include COPD, asthma, chronic bronchitis, cystic fibrosis, emphysema, and idiopathic pulmonary fibrosis.

Virus infection, and particularly rhinovirus infection, may increase the likelihood of developing chronic respiratory diseases and exacerbate existing chronic respiratory diseases (Saraya et al (2014)). Therefore the current invention advantageous reduces the risk of chronic respiratory diseases and/or reduces exacerbation by inhibiting rhinovirus infection and/or alleviating the inflammation caused by the rhinovirus infection.

In particular, in one embodiment the current invention reduces respiratory inflammation associated with rhinovirus infection.

COPD

Chronic obstructive pulmonary disease (COPD) is a lung disease characterized by chronic obstruction of lung airflow that interferes with normal breathing and is not fully reversible. The terms 'chronic bronchitis' and 'emphysema' are now included within the COPD diagnosis according to the World Health Organisation (WHO) definition. A COPD diagnosis is confirmed by a simple test called spirometry, which measures how deeply a person can breathe and how fast air can move into and out of the lungs. Such a diagnosis should be considered in any patient who has symptoms of cough, sputum production, or dyspnea (difficult or labored breathing), and/or a history of exposure to risk factors for the disease. Where spirometry is unavailable, the diagnosis of COPD may be made using other tools.

Clinical symptoms and signs, such as abnormal shortness of breath and increased forced expiratory time, can be used to help with the diagnosis. A low peak flow is consistent with COPD, as is a chronic cough and sputum production.

Asthma

Asthma is a chronic disease characterized by recurrent attacks of breathlessness, coughing and wheezing, which vary in severity and frequency from person to person. Symptoms may occur several times in a day or week in affected individuals, and for some people become worse during physical activity or at night.

During an asthma attack, the lining of the bronchial tubes swell, causing the airways to narrow and reducing the flow of air into and out of the lungs. Recurrent asthma symptoms frequently cause sleeplessness, daytime fatigue, reduced activity levels and school and work absenteeism.

Treatment of acute asthma symptoms is usually with an inhaled short-acting beta-2 agonist (such as salbutamol) and oral corticosteroids. In very severe cases, intravenous corticosteroids may be used.

Bifidobacteria

The present invention applies to any member of bifidobacteria, such as any member of the genus *Bifidobacterium*—which is a gram-positive anaerobic bacteria usually isolated from gastrointestinal flora.

While it is not intended that the present invention be limited to any particular species of bifidobacteria, in some particularly preferred embodiments the bifidobacteria is preferably *Bifidobacterium animalis*, more preferably from *Bifidobacterium animalis* subsp. *lactis* (i.e. "*Bifidobacterium lactis*"), more preferably *Bifidobacterium lactis* BL-04 finds use in the present invention. It is intended that the term includes species that have been reclassified (e.g., due to changes in the speciation of organisms as the result of genetic and other investigations) or renamed for marketing and/or other purposes.

*Bifidobacterium lactis* BL-04

*Bifidobacterium lactis* BL-04 (also referred to herein as "BL-04" and "Bl-04") is also known as *Bifidobacterium animalis* subsp. *lactis* BL-04—these terms are used herein interchangeably. *Bifidobacterium lactis* BL-04 has also been known as DGCC2908 and RB4825.

*Bifidobacterium lactis* BL-04 was originally isolated from a fecal sample from a healthy adult and is a commercial strain which has been used and deposited at the American Type Culture Collection (ATCC) safe deposit as strain SD5219 (see Barrangou R., et al; J. Bacteriol. 191:4144-4151(2009)). This is a publically available strain (available from DuPont).

The term "a fermentation product of a bifidobacteria" as used herein means a composition which results from culturing (e.g. fermenting) a bifidobacteria in a suitable media; or a supernatant or a fraction or a component thereof. In one embodiment the fermentation product of the bifidobacteria is the whole composition which results from culturing (e.g. fermenting) a bifidobacteria in a suitable media. The fermentation product may be dried prior to use.

The fermentation product of a bifidobacteria in one embodiment may comprise viable bifidobacteria. The fermentation product of bifidobacteria in another embodiment may be a cell-free fermentation product. A cell-free fermentation product may be a fermentation product of bifidobacteria which results from culturing (e.g. fermenting) bifidobacteria in a suitable media, which has been modified to remove and/or to inactive the bacterial cells to provide a cell-free fermentate. In another embodiment the fermentation product of bifidobacteria may comprise non-viable bifidobacteria which may be whole or lysated.

The term "cell-free" as used herein means that the fermentation product (preferably the fermentate) is substantially free of viable bacterial cells, typically containing less than about $10^5$ viable bacterial cells/mL fermentation product, less than about $10^4$ viable bacterial cells/mL fermentation product, less than about $10^3$ viable bacterial cells/mL fermentation product, less than about $10^2$ viable bacterial cells/mL fermentation product, or less than about 10 viable bacterial cells/mL fermentation product. Preferably, the fermentation product is substantially free of cells, typically containing less than about $10^5$ cells/mL fermentation product, less than about $10^4$ cells/mL fermentation product, less than about $10^3$ cells/mL fermentation product, less than about $10^2$ cells/mL fermentation product, or less than about 10 cells/mL fermentation product.

In one aspect, one or more cells may be separated from the fermentation product (e.g., fermentate). Such separation may be achieved by any means known in the art including by centrifuging and/or filtering. For example, the fermentation product can be filtered (one or several times in a multistep process) to remove such components as particulate matter, cells and the like. Alternatively or in addition, one or more cells and/or one of more spores may be separated from the fermentation product (e.g. fermentate) by centrifugation, thus producing a supernatant. Depending on the speed and duration of the centrifugation, the supernatant can be cell free (i.e., a cell-free supernatant) or the supernatant can contain cells, which can be filtered or further centrifuged to provide a cell-free supernatant.

In some aspects the fermentation product of a bifidobacteria may be a crude extract of the culture medium.

In some aspects the fermentation product of a bifidobacteria may comprise a mixture of constituents present following (e.g. at the end of) the culturing of bifidobacteria. Hence, the term fermentation product may comprise in addition to active ingredients other components such as particulate matter, solids, substrates not utilised during culturing, debris, media, and cell waste.

The term "cell-lysate of bifidobacteria" as used herein means the cellular debris and fluid produced by lysis of a bifidobacteria cell(s). Preferably the bifidobacteria cell(s) is/are isolated before being lysed.

Preferably the bifidobacteria cells are lysed by the following method: bifidobacteria are cultured at 37° C. anaerobically in MRS (or another suitably culture medium) supplemented with 0.05% cysteine; the bacterial cells are harvested by centrifugation (6000 rpm/5 min); the supernatant is aspirated and the pellet is optionally frozen at −70° C.; 1.5 ml pellet of bacterial cell culture to which 150 µl of T10E1 is added (10 mM Tris-HCl, pH 7.5; 1 mM EDTA) and vortexed to resuspend the cell pellet; 1 µl of Ready-Lyse™ Lysozyme (Epicentre, Vol 10, No. 3, 2003) is added to each resuspended pellet of bacteria (from 1 to 1.5 ml of culture); incubation at 37° C. for 30 minutes to overnight; 1 µl of Proteinase K (50 µg/µl) is diluted into 150 µl of 2× T&C Lysis Solution (both are provided in the MasterPure DNA Purification Kit, or sold separately) for each 1 to 1.5 ml of culture pelleted; 150 µl of the Proteinase K/Lysis solution is added to the sample and mixed thoroughly; incubation at 65° C. to 70° C. for 15 minutes, briefly vortexing every 5 minutes; cooling the samples to 37° C.; 1 µl of RNase A (5 µg/µl, provided in the kit, or sold separately) is added to each sample and mixed thoroughly; incubation at 37° C. for 30 minutes; the samples are placed on ice.

Alternative lysis methods for gram positive bacteria may be used to lyse the bifidobacteria—there are known to one skilled in the art.

Suitably, the fermentation product of bifidobacteria may be a fermentation product which is present in the supernatant phase isolated from a culture of the bifidobacteria cultured under the following conditions: 37° C. anaerobically in MRS (or another suitably medium) supplemented with 0.05% cysteine.

In one embodiment, the fermentation product may be obtainable (preferably obtained) by culturing the bacterium in a culture medium until the OD of the culture at λ600 reaches at least 0.6, preferably 0.6 to 1.5; optionally removing the bacteria by centrifugation and/or filtration (such as, for example, centrifugation at 25° C., 5 min, 3000 g and/or sterile-filtration) to result in a cell-free fermentate product comprising active ingredient(s).

Suitably, the fermentation product is obtainable (preferably obtained) using an MRS culture medium either with 1.0% sugar or without sugar. Suitably, the fermentation product is obtainable (preferably obtained) by culturing the bacteria at 37° C. Suitably, the fermentation product is obtainable (preferably obtained) by culturing the bacteria anaerobically.

The culturing of bifidobacteria can take place from about 1 to about 72 hours (h), from about 5 to about 60 h, or from about 10 to about 54 h or from 24 to 48 h.

In one aspect, the culturing can be carried out until nutrient depletion (preferably complete nutrient) occurs.

In one aspect, the culturing is for a time effective to reach the stationary phase of growth of the bacteria.

The temperature during the culturing can be from about 30 to about 50° C. from about 32 to about 40° C., or from about 34 to about 38° C., or at about 37° C.

The pH during the culturing can be at a pH from about 5 to about 9, from about 5 to about 6, from about 6 to about 7, from about 7 to about 8.

In one aspect, the culturing preferably takes place under aeration.

Batch and continuous culturing are known to a person of ordinary skill in the art. The fermentation product of the present invention may be prepared using batch or continuous culturing.

Suitably, the fermentation product may be harvested during or at the end of the culturing process In one aspect, the fermentation product of the present invention is harvested during or at the end of the exponential phase.

In one aspect, the fermentation product of the present invention is harvested at or during the stationary phase.

In one aspect of the present invention, the fermentation product may be produced in a vat under commercial conditions.

In one aspect, the culture is agitated and/or stirred during culturing (e.g. during fermentation).

In one aspect, the level of oxygenation is monitored and/or controlled during the culturing.

Suitably, the composition comprising bifidobacteria according to the present invention or the fermentation product of bifidobacteria or cell lysate of bifidobacteria may be in the form of a bacterial suspension, before or after freezing, or in the form of concentrates, either in dry, lyophilized or frozen form. Whatever the form used, the strain can be frozen.

In one embodiment the composition comprising bifidobacteria according to the present invention does not comprise a further microorganism, e.g. does not comprise a further probiotic bacterium.

In one embodiment the composition according the present invention consists of bifidobacteria, e.g. together with excipients, diluents or carriers.

Suitably, the composition comprising bifidobacteria and/or a fermentation product of bifidobacteria and/or a cell lysate of bifidobacteria according to the present invention may contain one or more additives. Suitably additives may be added during drying and/or during lyophilisation of the composition.

In one embodiment preferably the bifidobacteria in the composition and/or the fermentation product of the present invention are viable.

The term "viable" means a microorganism (bacterium) is metabolically active or able to differentiate.

In a preferred embodiment the composition comprises viable bifidobacteria.

In some embodiments the bifidobacteria (e.g. viable cells) are isolated from the medium in which it was cultured or the fermentation product prior to forming the composition comprising bifidobacteria of the present invention.

Dosage

The composition derivable from a bifidobacteria used in accordance with the present invention may comprise from $10^6$ to $10^{12}$ CFU of bacteria/g of composition, and more particularly from $10^8$ to $10^{12}$ CFU of bacteria/g of composition, preferably $10^9$ to $10^{12}$ CFU/g for the lyophilized form.

Suitably the composition derivable from a bifidobacteria used in accordance with the present invention may be administered at a dosage of from about $10^6$ to about $10^{12}$ CFU of bifidobacteria/dose, preferably about $10^8$ to about $10^{12}$ CFU of bifidobacteria/dose. By the term "per dose" it is meant that this amount of bifidobacteria is provided to a subject either per day or per intake, preferably per day. For example, if the bifidobacteria is to be administered in a food (for example in a yoghurt)—then the yoghurt will preferably contain from about $10^8$ to $10^{12}$ CFU of the bifidobacteria. Alternatively, however, this amount of bifidobacteria may be split into multiple administrations each consisting of a smaller amount of microbial loading—so long as the overall amount of bifidobacteria received by the subject in any specific time (for instance each 24 h period) is from about $10^6$ to about $10^{12}$ CFU of bifidobacteria, preferably $10^8$ to about $10^{12}$ CFU of *Bifidobacterium lactis* BL-04.

In accordance with the present invention an effective amount of bifidobacteria may be at least $10^6$ CFU of microorganism/dose, preferably from about $10^6$ to about $10^{12}$ CFU of microorganism/dose, preferably about $10^8$ to about $10^{12}$ CFU of microorganism/dose.

In one embodiment, preferably the bifidobacteria used in accordance with the present invention may be administered at a dosage of from about $10^6$ to about $10^{12}$ CFU of microorganism/day, preferably about $10^8$ to about $10^{12}$ CFU of microorganism/day. Hence, the effective amount in this embodiment may be from about $10^6$ to about $10^{12}$ CFU of microorganism/day, preferably about $10^8$ to about $10^{12}$ CFU of microorganism/day.

In one embodiment, preferably the bifidobacteria used in accordance with the present invention is administered at a dosage of from about $10^8$ to about $10^{10}$ CFU/day, preferably about $1\times10^9$ to $3\times10^9$ CFU/day, for example about $2\times10^9$ CFU of microorganism/day CFU stands for "colony-forming units".

Medication Modification

In one embodiment the composition derivable from a bifidobacteria and/or a fermentation product of bifidobacteria and/or a cell lysate of bifidobacteria according to the present invention may be used to modify medication (e.g. asthma/COPD alleviation or prevention medication) intake in a subject.

In one embodiment the term "modify" means "reduce".

The modification and/or reduction of medication means a modification or reduction compared with a placebo control.

The placebo control is not administered a composition derivable from a bifidobacteria and/or a fermentation product of bifidobacteria and/or a cell lysate of bifidobacteria according to the present invention. The placebo control may be administered sucrose.

The term "medication" may include medication for the treatment and alleviation of symptoms of chronic respiratory diseases such as asthma and COPD. This may include one or more of the following types of medication: inhaled short-acting beta-2 agonist (such as salbutamol), antihistamines, immunomodulators, oral corticosteroids and intravenous corticosteroids.

The composition derivable from a bifidobacteria and/or a fermentation product of bifidobacteria and/or a cell lysate of bifidobacteria according to the present invention maybe administered in or as a food product or may be administered as a pharmaceutically acceptable composition.

Further Microorganisms

In one embodiment of the present invention the composition derivable from a bifidobacteria and/or a fermentation product of a bifidobacteria and/or a cell lysate of a bifidobacteria according to the present invention may comprise at least one further probiotic microorganism, preferably at least one further probiotic bacterium.

In this specification the term 'probiotic microorganism' is defined as covering any non-pathogenic microorganism which, when administered live (e.g. viable) in adequate amounts, confer a health benefit on the host. These probiotic strains generally have the ability to survive the passage through the upper part of the digestive tract. They are non-pathogenic, non-toxic and exercise their beneficial effect on health on the one hand via ecological interactions with the resident flora in the digestive tract, and on the other hand via their ability to influence the immune system in a positive manner via the "GALT" (gut-associated lymphoid tissue). Depending on the definition of probiotics, these microorganism, when given in a sufficient number, have the ability to progress live through the intestine, however they do not cross the intestinal barrier and their primary effects are therefore induced in the lumen and/or the wall of the gastrointestinal tract. They then form part of the resident flora during the administration period. This colonization (or transient colonization) allows the probiotic microorganism to exercise a beneficial effect, such as the repression of potentially pathogenic micro-organisms present in the flora and interactions with the immune system of the intestine.

In certain embodiments, the further probiotic microorganism is a bacterium preferably a probiotic lactic acid bacterium and/or another probiotic bifidobacteria, preferably *Bifidobacterium animalis*, more preferably from *Bifidobacterium animalis* subsp. *lactis* (i.e. "*Bifidobacterium lactis*"), more preferably *Bifidobacterium lactis* BL-04.

In some embodiments the bacterium may be a bacterium from one or more of the following genera: *Lactococcus, Streptococcus, Pediococcus, Enterococcus, Leuconostoc, Carnobacterium, Propionibacterium, Bifidobacterium, Lactobacillus, Brevibacterium,* and *Vagococcus*. In one embodiment the at least one further probiotic microorganism is selected from the genera *Lactobacillus, Streptococcus, Enterococcus, Bifidobacterium* and *Saccharomyces*.

The further microorganism to be used in accordance with the present invention may be a microorganism which is generally recognised as safe and, which is preferably GRAS approved.

A skilled person will readily be aware of specific species and or strains of microorganisms from within the genera described herein which are used in the food and/or agricultural industries and which are generally considered suitable for human and/or animal consumption.

Hence, the composition of the present invention may contain a further microorganism (strain). The further microorganism used in accordance with the present invention is one which is suitable for human and/or animal consumption.

In one embodiment the further microorganism is from the genus *Lactobacillus* or the genus *Bifidobacterium* or is a mixture thereof.

In addition or in the alternative, the further microorganism may be a strain from the species *L. acidophilus, L. curvatus, L. rhamnosus, L. casei, L. paracasei, L. salivarius, B. lactis. B animalis, B. longum* and/or *B. bifidum.*

In one embodiment, the further microorganism may be a strain from the species *L. acidophilus, L. curvatus, L. salivarius* and/or *B. lactis.*

In one embodiment preferably the microorganism is from the genus *Streptococcus*. In one embodiment preferably the microorganism is from the genus *Enterococcus*. Preferably the microorganism may be a strain from the species *B. lactis* such as, for example, *B. lactis* 420 or *B. lactis* HN019.

For some embodiments the further microorganism may be a mixture of more than one probiotic microorganism (preferably more than one probiotic bacteria); a mixture of more than one bifidobacteria; or a mixture of one or more probiotic microorganism (preferably probiotic bacteria) and optionally one or more lactic acid bacteria. For example, the mixture may comprise one or more stains from *Bifidobacterium* spp and optionally one or more additional strains— such as a strain of *Lactobacillus* spp. The additional strain may be a catalase-negative strain, with a homofermentative metabolism giving rise to the production of lactic acid or may produce a bacteriocin, such as for example lactacin, active against other microorganisms. The further microorganism may be a *Lactobacillus* spp. such as *L. acidophilus, L. salivarius* and *L. curvatus* for example, for use in accordance with the present invention is preferably a gram-positive strain.

The bifidobacteria and/or the further strain—such as a *Lactobacillus* spp. such as *L. acidophilus, L. salivarius* and *L. curvatus*—for use in accordance with the present invention has a good resistance to pepsin, under acid pH conditions, a good resistance to pancreatin and/or a good tolerance to the bile salts.

In one embodiment, the further strain may be a *Lactobacillus* spp. such as *L. acidophilus* for example, according to the present invention may be a microorganism, preferably a *Lactobacillus* spp. such as *L. acidophilus* for example, which may be described as "hydrophobic", i.e. one having a strong affinity to polar or non-polar hydrophobic organic solvents, such as for example n-decane, chloroform, hexadecane or xylene. The *Lactobacillus acidophilus* according to the present invention may be *Lactobacillus acidophilus* PTA-4797. This strain of *Lactobacillus acidophilus* has been registered by Rhodia Chimie, 26, quai Alphonse Le Gallo, 92 512 BOULOGNE-BILLANCOURT Cedex France, in accordance with the Budapest Treaty at the American Type Culture Collection (ATCC), where it is recorded under registration number PTA-4797.

Immune System

As used herein, the term "cytokine" refers to a small protein (around 5-20 KDa) released by cells that has an effect on the interactions between cells, on communications between cells or on the behaviour of cells. Cytokines includes the interleukins, lymphokines and cell signal molecules, such as tumour necrosis factor and the interferons. Changes in cytokine amount may trigger responses such as inflammation and immune response to infections in the body. As used herein, the term "chemokine" refers to a type of small cytokines which have the ability to induce directed chemotaxis (the movement of an organism in response to a chemical stimulus) in nearby responsive cells.

As used herein, the term "biomarker" refers to a broad subcategory of medical signs which can be measured accurately and reproducibly. They are used as objective indications of medical state observed from outside the patient. Biomarkers can be measured and evaluated as an indicator of normal biological processes, pathogenic processes, or pharmacologic responses to a therapeutic intervention. Both cytokines and chemokines can be used as biomarkers. Biomarkers can be measured in the respiratory tract, in the nasal passage, in a nasal lavage or in the blood or cerebral fluid for example. Measurements of biomarkers can take place in vivo and in vitro.

As used herein, the "modulate" means to change or vary. Modulating the immune system can include increasing or decreasing or changing the amount or level of any aspect of the immune system. In particular as used herein modulating the immune system may refer to the amount of cytokines or chemokines present compared to a control or placebo. In one embodiment, the cytokines or chemokines are present in the respiratory tract, in the nasal passage, in a nasal lavage or in the blood. In one embodiment the amount of one or more cytokine or chemokine is reduced. In another embodiment, the amount of one or more cytokines or chemokines is affected, such as decreased.

In one embodiment of the present invention, modulation of the immune system decreases the level of at least one inflammatory biomarker in a subject. Preferably said biomarkers include at least one cytokine or chemokine.

Preferably, the cytokine is a cytokine that mediates inflammatory response.

Preferably, the chemokine is a chemokine that mediates inflammatory response.

Preferably the chemokine is an inflammatory chemokine that attracts inflammatory cells to the airways. This includes but is not limited to IL-8, MCP-1 IP-10, GM-CSF, MIP-3alpha and G-CSF.

Preferably the cytokine includes but is not limited to TNF-alpha, IL-1beta and IL-6.

Some cytokines and chemokines may have both cytokine and chemokine function. This includes but is not limited to IL-8.

Most preferably the methods and uses of the present invention reduce the level of at least one biomarker present in the subject. Most preferably said biomarker is a chemokine and/or a cytokine, most preferably an inflammatory cytokine and/or an inflammatory chemokine. In a preferred embodiment, the levels of cytokines and/or chemokines are reduced in the lower respiratory tract. The cytokines and/or chemokines can be measured from a bronchoalveolar lavage or nasal lavage for example. Most preferably the cytokine measured is IL-8. As this cytokine is associated with inflammation, reduced levels of IL-8 indicate reduced inflammation in the subject.

A biomarker may be present in the subject anywhere, and measured anywhere, for example in the respiratory tract, in the nasal passage, in a nasal lavage or in the blood or cerebral fluid for example. Measurements of biomarkers can take place in vivo and in vitro.

Preferably in the present invention the decreased level of cytokines and/or chemokines leads to decreased exhaled Nitric Oxygen (eNO). Measuring the amount of eNO may be used to measure inflammation in the lower airways.

Most particularly, the methods and uses of the present invention reduce the level of IL-8.

In another embodiment, the methods and uses of the present invention reduce the level of MCP-1.

In another embodiment, the methods and uses of the present invention reduce the level of IL-1beta.

In another embodiment, the methods and uses of the present invention reduce the level of any one or two or all of IL-8, MCP-1 and IL-1beta.

IL-8 is an inflammatory marker. It is known to mediate neutrophilic, lymphocytic and eosinophilic inflammation with airway hyperresponsiveness and airway remodeling that are hallmarks of asthma (Wark et al. 2002; Proud 2011).

Innate immune system is responsible for generating the inflammatory cytokines and chemokines during the first 4 days of infection (Proud 2011). IL-8 is thus a marker of innate immune system function.

The term "Innate immune system" refers to aspects of the immune system which occurs naturally as a result of a person's genetic constitution or physiology and does not arise from a previous infection or vaccination. In particular in the context of the current invention, the innate immune system includes aspects of the immune system which respond to virus infection and produces cytokines that initiate anti-viral defences and alert innate immune cells and induces adaptive immune response.

The adaptive immune system (or specific immune response) consists of antibody responses and cell-mediated responses, which are carried out by different lymphocyte cells, B cells and T cells, respectively.

Adaptive immunity creates a specific and strong response against the pathogen and includes various cell types.

Cluster of Differentiation (CD) is a classification of identifying different cell types.

CD antigens are on the surface of the cells and can be identified by using antibodies and flow cytometer. CD+ means that antigen is present, CD− means that antigen is not present.

The adaptive immune response is initiated by dendritic cells that present antigens to lymphocytes (CD3+ cells).

A subpopulation of lymphocytes is called T-helper cells (CD3+CD4+) that are part of the immune system. These cells can be identified from the blood if they are not monocytes (CD14-), not B-cells (CD19-), and are CD3+ CD4+

T-helper cells positive for rhinoviruses can be identified by using MHC-II tetramers that are loaded with HRV39 specific peptides ("HRV39 specific").

Chemokine Receptor CCR5 targets T-helper cells to site of infection, including respiratory tract, from blood.

In a preferred embodiment, CD3+CD4+CD14-CD19-tetramer+ cells ("HRV39 specific T-helper cells") and CD3+ CD4+CD14-CD19-tetramer+ CCR5+ cells ("HRV39 specific CCR5+T-helper cells") may be identified from blood samples from the subject.

In a preferred embodiment, the compositions, methods and uses of the present invention lead to an increase in virus specific T-helper cells in a subject, compared to a placebo. In a most preferred embodiment, there is an increase in T-helper cells positive for rhinoviruses in a subject, compared to a placebo. Such cells are known to migrate to the site of viral infections, such as the respiratory mucosa. Furthermore, such cells confer protection against future rhinovirus infections.

Subject

The term "subject", as used herein, means an animal. Preferably, the subject is a mammal, including for example livestock (including cattle, horses, pigs, chickens and sheep), and humans. In some aspects of the present invention the animal is a companion animal (including pets), such as a dog or a cat for instance. In some aspects of the present invention, the subject may suitably be a human.

In one embodiment the subject is a human.
In one embodiment the subject may be female.
In one embodiment the subject may be male.
In one embodiment the subject is a child. The term "child" as used herein means a human of less than 16 years of age.
In one embodiment the subject is a human that is 16 years of age or older.
In one embodiment the subject is a human that is 18 years of age or older.
In one embodiment the subject is not an immunocompromised subject.
In one embodiment the subject is a healthy subject.
In one embodiment the subject has a fully developed and non-compromised immune system.
In one embodiment the subject suffers from a chronic respiratory disease.
In one embodiment the subject suffers from asthma.
In a further embodiment the subject suffers from COPD.
In a further embodiment the subject is susceptible to asthma or COPD. This can be due to a number of reasons include one or more of genetics, exposure to pathogens, exposure to poisons and exposure to cigarette smoke.

Advantages

The inventors have surprisingly found that use of a bifidobacteria significantly reduces the incidence, duration and/or severity of viral effects, in particular inflammation caused by virus infections, when compared to placebo in healthy adults. This indicates that bifidobacteria can modulate the innate immune response in healthy adults. This has been demonstrated by a decrease in specific cytokines in IL-8, IL-1beta, MCP-1

Furthermore, the inventors have found that use of a composition derivable from bifidobacteria significantly inhibits the replication of viruses and alleviates inflammation caused by the virus infection. This reduces the risk of development and exacerbation of chronic respiratory diseases such as asthma and COPD.

In particular, use of a composition derivable from a bifidobacteria significantly reduces the risk of development and exacerbation of asthma and COPD that are associated with rhinovirus infections. As these illnesses may have a long term effect on the quality of life of a subject, including increasing morbidity, the current invention is highly advantageous.

Surprisingly, the inventors have found that a composition derivable from a bifidobacteria has an influence on adaptive immune system.

Particularly, said composition increases the number of HRV39 specific CCR5+T-helper cells that function to migrate to site of viral infections, such as respiratory mucosa. As the increase was observed 21 days after initial infection the increase number of HRV39 specific CCR5+T-helper cells confers better protection against subsequent HRV infections. A reduction in HRV infections reduces the chance of develop and exacerbation of chronic respiratory diseases such as asthma and COPD, because these disease are known to be associated with HRV infections (Saraya et al. 2014).

Surprisingly this effect has been found using a single strain of a bifidobacteria, preferably *Bifidobacterium animalis*, more preferably from *Bifidobacterium animalis* subsp. *lactis*, more preferably *Bifidobacterium lactis* BL-04, alone or without a further microorganism in the composition.

One advantage of the present invention is that the use of the composition of and methods of the invention significantly reduces the incidence, duration and/or severity of symptoms of virus infection. This applies to healthy individuals and also individuals suffering from chronic respiratory diseases or those who are susceptible to chronic respiratory diseases.

The present inventors have found that the advantageous effects observed herein can be obtained using one bifidobacteria strain alone. This can lead to many advantages including simplifying the production of the supplement and/or reducing costs of the manufacture of the supplement and the supplement itself.

A further advantage is that one bifidobacteria strain can be used without additional probiotic bacteria—this has the advantage that it simplifies the stability issues with regard to the supplement. Therefore one advantage of the present invention is that the composition derivable from a bifidobacteria strain the (e.g. alone or without the presence of another microorganism) is easier to stabilise as the skilled person is only concerned with the stability of a single bacterium rather than more than one bacterium.

In addition or alternatively the use of a single bacterial strain in a composition can have the advantage of reducing cost-in-use of the composition compared with mixed strain compositions.

A significant further advantage of the present invention is that the inventors have surprising found that use of a composition derivable from a bifidobacteria in accordance with the present invention can be used to modify or reduce the medication intake in a subject, in particular a subject suffering from chronic respiratory disease.

Medicament

The term "medicament" as used herein in relation to the invention encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example) and natural remedies.

Treatment

It is to be appreciated that all references herein to treatment include palliative and prophylactic treatment.

Substantially Pure Form and/or Isolated Form

For some aspects the microorganism and/or fermentation product and/or cell lysate according to the present invention may be in a substantially pure form or may be in an isolated form.

The term "substantially pure form" is used to indicate that the microorganism and/or fermentation product and/or cell lysate according to the present invention is present at a high level. When the microorganism and/or fermentation product and/or cell lysate is in a substantially pure form, the microorganism and/or fermentation product and/or cell lysate is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration.

At very high levels (e.g. at levels of more than 90%, of more than 95% or of more than 99%) the microorganism and/or fermentation product and/or cell lysate may be regarded as being "isolated".

Biologically active substances of the present invention (including polypeptides, nucleic acid molecules, carbohydrates identified/identifiable via screening, lipids identified/identifiable via screening, moieties identified/identifiable via screening, etc.) may be provided in a form that is substantially free of one or more contaminants with which the substance might otherwise be associated. Thus, for example, they may be substantially free of one or more potentially contaminating polypeptides and/or nucleic acid molecules. They may be provided in a form that is substantially free of other cell components (e.g. of cell membranes, of cytoplasm, etc.). When a composition is substantially free of a given contaminant, the contaminant will be at a low level (e.g. at a level of less than 10%, less than 5% or less than 1% on the dry weight/dry weight basis set out above).

Combination with Other Components

The bifidobacteria, preferably *Bifidobacterium animalis*, more preferably from *Bifidobacterium animalis* subsp. *lactis*, more preferably *Bifidobacterium lactis* BL-04 and/or fermentation product thereof and/or cell lysate thereof for use in the present invention may be used in combination with other components. Thus, the present invention also relates to combinations. The bifidobacteria, preferably from *Bifidobacterium*, more preferably *Bifidobacterium animalis*, more preferably from *Bifidobacterium animalis* subsp. *lactis*, more preferably *Bifidobacterium lactis* BL-04 and/or fermentation product thereof and/or cell lysate thereof may be referred to herein as "the composition of the present invention".

The combination of the present invention comprises the composition of the present invention and another component which is suitable for animal or human consumption and is capable of providing a medical or physiological benefit to the consumer.

Other components of the combinations of the present invention include polydextrose, such as Litesse®, and/or a maltodextrin and/or lactitol. These other components may be optionally added to the composition to assist the drying process and help the survival of the microorganisms.

Further examples of other suitable components include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

In one embodiment the microorganism and/or fermentation product and/or cell lysate thereof may be encapsulated.

In one preferred embodiment the microorganism and/or fermentation product and/or cell lysate thereof for use in the present invention may be used in combination with one or more lipids.

For example, the microorganism and/or fermentation product and/or cell lysate thereof for use in the present invention may be used in combination with one or more lipid micelles. The lipid micelle may be a simple lipid micelle or a complex lipid micelle.

The lipid micelle may be an aggregate of orientated molecules of amphipathic substances.

The lipid micelles may be an aggregate, of colloidal dimensions, of orientated molecules of amphipathic substances existing in equilibrium in solution with the chemical species from which it is formed. Micelles are generally electrically charged. In aqueous solution the individual molecules of the micellar aggregate are oriented with their polar groups pointing towards the aqueous medium and their hydrophobic moiety directed into the centre of the micelle. The lipid micelles may comprise a lipid and/or an oil.

As used herein the term "thickener or gelling agent" refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilising them.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers. Aeration can occur in a three-phase system where air is entrapped by liquid oil then stabilised by agglomerated fat crystals stabilised with an emulsifier. Emulsifiers have a polar group with an affinity for water (hydrophilic) and a non-polar group which is attracted to oil (lipophilic). They are absorbed at the interfaces of the two substances, providing an interfacial film acting to stabilise the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilise water-in-oil emulsions. High HLB values are assigned to hydrophilic emulsifiers, typically used in oil-in-water emulsions. These values are derived from simple systems. Because foods often contain other ingredients that affect the emulsification properties, the HLB values may not always be a reliable guide for emulsifier selection.

As used herein the term "binder" refers to an ingredient (e.g. a food ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

The term "crystal modifier" as used herein refers to an ingredient (e.g. a food ingredient) that affects the crystallisation of either fat or water. Stabilisation of ice crystals is important for two reasons. The first is directly related to the product stability from a separation standpoint. The more freeze/thaw cycles a product encounters, the larger the ice crystals become. These large crystals can break down product structure, either naturally occurring, as in the case of cell walls, or that which is created by "elation". Because the water is no longer held in place, the product may exhibit syneresis, or weeping, after thawing. Secondly, in the case of a product which is consumed frozen, these large crystals result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes).

Preferably, when the composition of the present invention when admixed with any other components, the microorganisms remain viable.

As used herein the term "component suitable for animal or human consumption" means a compound which is or can be added to the composition of the present invention as a supplement which may be of nutritional benefit, a fibre substitute or have a generally beneficial effect to the consumer. The ingredients can be used in a wide variety of products that require gelling, texturising, stabilising, suspending, film-forming and structuring, retention of juiciness, without adding unnecessary viscosity. Preferably, the ingredients will be able to improve the shelf life and stability of the viable culture.

The components may be prebiotics such as alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, palatinose, isomalto-oligosaccharides, gluco-oligosaccharides and xylo-oligosaccharides.

The optimum amount of the composition to be used in the combination of the present invention will depend on the product to be treated and/or the method of contacting the product with the composition and/or the intended use for the same. The amount of viable microorganism used in the compositions should be a sufficient amount to be effective and to remain sufficiently effective in improving the aroma, flavour, mildness, consistency, texture, body, mouth feel, viscosity, structure and/or organoleptic properties, nutrition and/or health benefits of food products containing said composition. This length of time for effectiveness should extend up to at least the time of utilisation of the product.

Concentrates

The compositions for use in the present invention may be in the form of concentrates.

Typically these concentrates comprise a substantially high concentration of a bifidobacteria, preferably *Bifidobacte-*

*rium animalis*, more preferably from *Bifidobacterium animalis* subsp. *lactis*, more preferably *Bifidobacterium lactis* BL-04 and/or fermentation product and/or cell lysate thereof.

Powders, granules and liquid compositions in the form of concentrates may be diluted with water or resuspended in water or other suitable diluents, for example, an appropriate growth medium such as milk or mineral or vegetable oils, to give compositions ready for use.

The combinations of the present invention in the form of concentrates may be prepared according to methods known in the art.

In one aspect of the present invention the product is contacted by a composition in a concentrated form. Preferably, the product is contacted by a spray-dried and/or resuspended composition.

The compositions of the present invention may be in powder form.

The compositions of the present invention may be dried—such as spray-dried or freeze-dried by methods known in the art.

Typical processes for making particles using a spray drying process involve a solid material which is dissolved in an appropriate solvent (e.g. a culture of a micro-organism in a fermentation medium). Alternatively, the material can be suspended or emulsified in a non-solvent to form a suspension or emulsion. Other ingredients (as discussed above) or components such as anti-microbial agents, stabilising agents, dyes and agents assisting with the drying process (sometimes referred to as drying agents) may optionally be added at this stage.

The solution then is atomised to form a fine mist of droplets. The droplets immediately enter a drying chamber where they contact a drying gas. The solvent is evaporated from the droplets into the drying gas to solidify the droplets, thereby forming particles. The particles are then separated from the drying gas and collected.

Products

Any product which can benefit from the composition may be used in the present invention. These include but are not limited to dairy foods and dairy food-derived products, dietary supplements and pharmaceutical products.

By way of example, the composition of the present invention can be used as an ingredient to soft drinks, a fruit juice or a beverage comprising whey protein, health teas, cocoa drinks, milk drinks, bifidobacteria product, lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is preferably admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a viable microorganism.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

Preferably, the composition is used to ferment milk or sucrose fortified milk or media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

For some aspects the microorganisms according to the present invention or composition according to the present invention are used as—or in the preparation of—animal feeds, such as livestock feeds, in particular poultry (such as chicken) feed, or pet food.

Food Ingredient

The composition of the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The composition of the present invention may be—or may be added to—food supplements such as dietary supplements.

Functional Foods

The composition of the present invention may be—or may be added to—functional foods.

As used herein, the term "functional food" means food which is capable of providing not only a nutritional effect, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects beyond basic nutritional effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Probiotic

For some applications, it is believed that the viable bifidobacteria, preferably *Bifidobacterium animalis*, more preferably from *Bifidobacterium animalis* subsp. *lactis*, more preferably *Bifidobacterium lactis* BL-04 in the composition of the present invention can exert a probiotic culture effect. It is also within the scope of the present invention to add to the composition of the present invention further probiotic and/or prebiotics. Here, a prebiotic is: "a non-digestible food ingredient that beneficially affects the host by selectively stimulating the growth and/or the activity of one or a limited number of beneficial bacteria".

The term "probiotic culture" as used herein defines live microorganisms (including bacteria or yeasts for example) which, when for example ingested or locally applied in sufficient numbers, beneficially affects the host organism, i.e. by conferring one or more demonstrable health benefits on the host organism. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut.

Whilst there are no lower or upper limits for probiotic intake, it has been suggested that at least $10^6$-$10^{12}$, preferably at least $10^6$-$10^{10}$, preferably $10^8$-$10^9$, cfu as a daily dose will be effective to achieve the beneficial health effects in a host organism, such as a human.

In addition to the probiotic effect the microorganism according to the present invention may have, it is also within the scope of the present invention to provide prebiotics as other compounds which can be included in a combination along with the composition. The prebiotic component of the combination comprising the composition of the present invention are characterised with slow fermentation in the large bowel. Such prebiotics can exert a positive effect on the gut flora, specifically in the left side of the colon, an area of the gut which is especially prone to disorders in particular bowel cancer and ulcerative colitis.

Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and galacto-oligosaccharides (GOS) and transgalacto-oligosaccharides (TOS). Other suitable, prebiotics include palatinoseoligosaccharide, soybean oligosaccharide, gentiooligosaccharide, xylooligomers, non-degradable starch, lactosaccharose, lactulose, lactitol, maltitol, polydextrose (i.e. Litesse®) or the like.

In one embodiment the present invention relates to the combination of a bifidobacteria, preferably *Bifidobacterium animalis*, more preferably from *Bifidobacterium animalis* subsp. *lactis*, more preferably *Bifidobacterium lactis* BL-04 and/or fermentation product thereof and/or cell lysate thereof according to the present invention with a prebiotic.

The prebiotic may be administered simultaneously with (e.g. in admixture together with or delivered simultaneously by the same or different routes) or sequentially to (e.g. by the same or different routes) the microorganism according to the present invention and/or fermentation product thereof and/or cell lysate thereof.

Synbiotics

The present invention also contemplates using both pre- and probiotics as ingredients in a combination along with the composition of the present invention which when combined, become synbiotics. The purpose of this is to combine the effects of the beneficial bacteria and the stimulation of the body-own beneficial bacteria. There is a high potential in the development and the consumption of such mixtures, since some of these may well show powerful synergistic nutritional and/or health effects.

Thus the composition of the present invention may be specifically designed to contain different components which can provide a synbiotic effect to the consumer.

Pharmaceutical

The composition of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

Pharmaceutical Ingredient

The microorganisms of the present invention may be used as pharmaceutical ingredients. Here, the composition may be the sole active component or it may be at least one of a number (i.e. 2 or more) of active components.

The pharmaceutical ingredient may be in the form of a solution or as a solid—depending on the use and/or the mode of application and/or the mode of administration.

Forms

The microorganism of the present invention and/or fermentation product thereof and/or cell lysate thereof may be used in any suitable form—whether when alone or when present in a combination with other components or ingredients. Likewise, combinations comprising the composition of the present invention and other components and/or ingredients (i.e. ingredients—such as food ingredients, functional food ingredients or pharmaceutical ingredients) may be used in any suitable form.

The microorganism of the present invention or composition of the present invention may be used in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even fibre beverages.

Further examples are in the form of a cream for example. For some aspects the microorganism and/or a metabolite thereof may be included in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

Aspects of the present invention will now be described by way of numbered paragraphs.

1. A composition derivable from a bifidobacteria (preferably *Bifidobacterium animalis*, more preferably from *Bifidobacterium animalis* subsp. *lactis*, more preferably *Bifidobacterium lactis* BL-04) for use in modulating the immune system in a subject by affecting viral action and/or viral effects in said subject.

2. The composition for use according to paragraph 1 wherein the composition derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably a *Bifidobacterium* lactic bacterium, more preferably *Bifidobacterium lactis* BL04) and/or a cell lysate of a bifidobacteria (preferably a *Bifidobacterium* lactic bacterium, more preferably *Bifidobacterium lactis* BL04).

3. The composition for use according to paragraph 1 or paragraph 2 wherein affecting viral action and/or viral effects include inhibiting virus replication and/or alleviation of inflammation caused by the virus infection.

4. The composition for use according to any one of paragraphs 1 to 3 wherein said virus is one or more of a rhinovirus, coronavirus, parainfluenza virus, adenovirus, enterovirus, or respiratory syncytial virus, preferably at least a human rhinovirus (HRV).

5. The composition for use according to any one of paragraphs 1 to 4, wherein modulation of the immune system modulates biomarker levels in the subject, preferably reduces biomarker levels in the subject.

6. The composition for use according to paragraph 5 wherein said biomarkers are cytokines and/or chemokines.

7. The composition for use according to any one of paragraphs 5 to 6 wherein said biomarkers are IL-8 and/or IL-1beta and/or MCP-1.

8. The composition for use according to any one of paragraphs 1 to 7 wherein modulation of the immune system involves modulation of the innate immune system, the adaptive immune system or both.

9. The composition for use according to any one of paragraphs 1 to 8 wherein modulation of the immune system increases the number of virus specific T-helper cells.

10. The composition for use according to any one of paragraphs 1 to 9 wherein modulation of the immune system reduces levels of IL-8 and/or IL-1beta and/or MCP-1.

11. The composition for use according to any one of paragraphs 1 to 10 wherein the subject is a human subject.

12. The composition for use according to any one of paragraphs 1 to 11 wherein the subject is a human child.

13. The composition for use according to any one of paragraphs 1 to 11 wherein affecting viral action and/or viral effects includes alleviation of inflammation caused by virus infection and causes alleviation of the symptoms of virus infection including one or more of the group consisting of:

respiratory inflammation, throat soreness, sneezing, blocked nose, runny nose, a cough, coughing with chest congestion and coughing with wheezing.

14. The composition for use according to any one of the preceding paragraphs, wherein the use is prophylactic.

15. The composition for use according to any one of the preceding paragraphs, wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably *Bifidobacterium animalis*, more preferably from *Bifidobacterium animalis* subsp. *lactis*, more preferably *Bifidobacterium lactis* BL-04)/per day, preferably wherein said composition is formulated at a dose of around or at $2\times10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

16. The composition for use according to any one of the preceding paragraphs, comprising at least one further probiotic microorganism.

17. The composition for use according to paragraph 16, wherein the at least one further probiotic microorganism is selected from the genera *Lactobacillus, Streptococcus, Enterococcus*, another bifidobacteria and *Saccharomyces*.

18. The composition for use according to any one of the preceding paragraphs, wherein said composition is a medicament, a food product or a dietary supplement.

19. The composition for use according to any one of the preceding paragraphs, wherein the bacteria is formulated as a dietary supplement.

20. A method of modulating the immune system in a subject by affecting viral action and/or viral effects in said subject comprising use of a composition to be administered to and/or ingested by said subject; said composition being derivable from a bifidobacteria (preferably *Bifidobacterium animalis*, more preferably from *Bifidobacterium animalis* subsp. *lactis*, more preferably *Bifidobacterium lactis* BL-04); preferably wherein the composition derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably *Bifidobacterium animalis*, more preferably from *Bifidobacterium animalis* subsp. *lactis*, more preferably *Bifidobacterium lactis* BL-04) and/or a cell lysate of a bifidobacteria (preferably *Bifidobacterium animalis*, more preferably from *Bifidobacterium animalis* subsp. *lactis*, more preferably *Bifidobacterium lactis* BL-04); and/or preferably wherein affecting viral action and/or viral effects include inhibiting virus replication and/or alleviation of inflammation caused by the virus infection.

21. The method according to paragraph 20 wherein said virus is a rhinovirus, coronavirus, parainfluenza virus, adenovirus, enterovirus, or respiratory syncytial virus.

22. The method according to paragraph 20 wherein said virus is a rhinovirus, preferably a human rhinovirus (HRV).

23. The method according to any one of paragraphs 20 to 22, wherein modulation of the immune system modulates biomarker levels in the subject, preferably reduces biomarker levels in the subject.

24. The method according to paragraph 23 wherein said biomarkers are cytokines and/or chemokines.

25. The method according to any one of paragraphs 23 to 24 wherein said biomarkers are IL-8 and/or IL-1beta and/or MCP-1.

26. The method according to any one of paragraphs 20 to 25 wherein modulation of the immune system involves modulation of the innate immune system, the adaptive immune system or both.

27. The method according to any one of paragraphs 20 to 26 wherein modulation of the immune system increases the number of virus specific T-helper cells.

28. The method according to any one of paragraphs 20 to 27 wherein modulation of the immune system reduces levels of IL-8 and/or IL-1beta and/or MCP-1.

29. The method according to any one of paragraphs 20 to 28 wherein the subject is a human subject.

30. The method according to any one of paragraphs 20 to 29 wherein the subject is a human child.

31. The method according to any one of paragraphs 20 to 30 wherein alleviation of inflammation caused by virus infection causes alleviation of the symptoms of virus infection, including one or more of the group consisting of: respiratory inflammation, throat soreness, sneezing, blocked nose, runny nose, a cough, coughing with chest congestion and coughing with wheezing.

32. The method according to any one of paragraphs 20 to 31, wherein the method is prophylactic.

33. The method according to any one of paragraphs 20 to 32, wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably *Bifidobacterium animalis*, more preferably from *Bifidobacterium animalis* subsp. *lactis*, more preferably *Bifidobacterium lactis* BL-04)/per day.

34. The method according to paragraph 33 wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of around or at $2\times10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

35. The method according to any one of paragraphs 20 to 34, comprising administering and/or ingesting at least one further probiotic microorganism.

36. The method according to paragraph 35, wherein the at least one further probiotic microorganism is selected from the genera *Lactobacillus, Streptococcus, Enterococcus*, another bifidobacteria and *Saccharomyces*.

37. The method according to any one of paragraphs 20 to 36, wherein the composition is formulated a medicament, a food product or a dietary supplement.

38. The method according to any one of paragraphs 20 to 37, wherein the composition is formulated as a dietary supplement.

39. Use of a composition derivable from a bifidobacteria (preferably *Bifidobacterium animalis*, more preferably from *Bifidobacterium animalis* subsp. *lactis*, more preferably *Bifidobacterium lactis* BL-04) in the manufacture of a composition for modulating the immune system in a subject by affecting viral action and/or viral effects in said subject; preferably wherein the composition derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably *Bifidobacterium animalis*, more preferably from *Bifidobacterium animalis* subsp. *lactis*, more preferably *Bifidobacterium lactis* BL-04) and/or a cell lysate of a bifidobacteria (preferably *Bifidobacterium animalis*, more preferably from *Bifidobacterium animalis* subsp. *lactis*, more preferably *Bifidobacterium lactis* BL-04); and/or preferably wherein affecting viral action and/or viral effects include inhibiting virus replication and/or alleviation of inflammation caused by the virus infection.

40. The use according to paragraph 39 wherein said virus is a rhinovirus, coronavirus, parainfluenza virus, adenovirus, enterovirus, or respiratory syncytial virus.

41. The use according to paragraph 39 wherein said virus is a rhinovirus, preferably a human rhinovirus (HRV).

42. The use according to any one of paragraphs 39 to 41, wherein modulation of the immune system modulates biomarker levels in the subject, preferably reduces biomarker levels in the subject.

43. The use according to paragraph 42 wherein said biomarkers are cytokines and/or chemokines.

44. The use according to any one of paragraphs 39 to 43 wherein said biomarkers are IL-8 and/or IL-1beta and/or MCP-1.

45. The use according to any one of paragraphs 39 to 44 wherein modulation of the immune system involves modulation of the innate immune system, the adaptive immune system or both.

46. The use according to any one of paragraphs 39 to 45 wherein modulation of the immune system increases the number of virus specific T-helper cells.

47. The use according to any one of paragraphs 39 to 46 wherein modulation of the immune system reduces levels of IL-8 and/or IL-1beta and/or MCP-1.

48. The use according to any one of paragraphs 39 to 47 wherein the subject is a human subject.

49. The use according to any one of paragraphs 39 to 48 wherein the subject is a human child.

50. The use according to any one of paragraphs 39 to 49 wherein alleviation of inflammation caused by virus infection causes alleviation of the symptoms of virus infection, including one or more of the group consisting of: respiratory inflammation, throat soreness, sneezing, blocked nose, runny nose, a cough, coughing with chest congestion and coughing with wheezing.

51. The use according to any one of paragraphs 39 to 50, wherein the use is prophylactic.

52. The use according to any one of paragraphs 39 to 51, wherein the composition comprising a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably *Bifidobacterium animalis*, more preferably from *Bifidobacterium animalis* subsp. *lactis*, more preferably *Bifidobacterium lactis* BL-04)/per day.

53. The use according to paragraph 52 wherein said composition is formulated at a dose of around or at $2 \times 10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

54. The use according to any one of paragraphs 39 to 53, wherein the composition comprises at least one further probiotic microorganism.

55. The use according to paragraph 54, wherein the at least one further probiotic microorganism is selected from the genera *Lactobacillus, Streptococcus, Enterococcus*, another bifidobacteria and *Saccharomyces*.

56. The use according to any one of paragraphs 39 to 55, wherein said composition is a medicament, a food product or a dietary supplement.

57. The use according to any one of paragraphs 39 to 56, wherein the bacteria is formulated as a dietary supplement.

58. A composition derivable from a bifidobacteria (preferably *Bifidobacterium animalis*, more preferably from *Bifidobacterium animalis* subsp. *lactis*, more preferably *Bifidobacterium lactis* BL-04) for use in reducing the risk of development and exacerbation of chronic respiratory diseases in a subject; preferably wherein the composition derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably *Bifidobacterium animalis*, more preferably from *Bifidobacterium animalis* subsp. *lactis*, more preferably *Bifidobacterium lactis* BL-04) and/or a cell lysate of a bifidobacteria (preferably *Bifidobacterium animalis*, more preferably from *Bifidobacterium animalis* subsp. *lactis*, more preferably *Bifidobacterium lactis* BL-04).

59. The composition for use according to paragraph 58 wherein risk of development and exacerbation of chronic respiratory diseases is reduced due to modulation of the immune system by affecting viral action and/or viral effects; preferably inhibiting virus replication and/or alleviation of inflammation caused by the virus infection.

60. The composition for use according to paragraph 58 or 59 wherein said chronic respiratory diseases are asthma and/or COPD.

61. The composition for use according to any one of paragraphs 58-60 wherein said virus is a rhinovirus, coronavirus, parainfluenza virus, adenovirus, enterovirus, or respiratory syncytial virus.

62. The composition for use according to paragraph 61 wherein said virus is a rhinovirus, preferably a human rhinovirus (HRV).

63. The composition for use according to any one of paragraphs 59 to 62, wherein modulation of the immune system modulates biomarker levels in the subject, preferably reduces biomarker levels in the subject.

64. The composition for use according to paragraph 63 wherein said biomarkers are cytokines and/or chemokines.

65. The composition for use according to any one of paragraphs 63 to 64 wherein said biomarkers are IL-8 and/or IL-1beta and/or MCP-1.

66. The composition for use according to any one of paragraphs 59 to 65 wherein modulation of the immune system involves modulation of the innate immune system, the adaptive immune system or both.

67. The composition for use according to any one of paragraphs 59 to 66 wherein modulation of the immune system increases the number of virus specific T-helper cells.

68. The composition for use according to any one of paragraphs 59 to 67 wherein modulation of the immune system reduces levels of IL-8 and/or IL-1beta and/or MCP-1.

69. The composition for use according to any one of paragraphs 58 to 68 wherein the subject is a human subject.

70. The composition for use according to any one of paragraphs 58 to 69 wherein the subject is a human child.

71. The composition for use according to any one of paragraphs 58 to 70 wherein alleviation of inflammation caused by virus infection causes alleviation of the symptoms of virus infection, including one or more of the group consisting of: respiratory inflammation, throat soreness, sneezing, blocked nose, runny nose, a cough, coughing with chest congestion and coughing with wheezing.

72. The composition for use according to any one of the paragraphs 58 to 71, wherein the use is prophylactic.

73. The composition for use according to any one of paragraphs 58 to 72, wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably *Bifidobacterium animalis*, more preferably from *Bifidobacterium animalis* subsp. *lactis*, more preferably *Bifidobacterium lactis* BL-04)/per day.

74. The composition for use according to paragraph 73 wherein said composition is formulated at a dose of around or at $2\times10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

75. The composition for use according to any one of paragraphs 58 to 74, comprising at least one further probiotic microorganism.

76. The composition for use according to paragraph 75, wherein the at least one further probiotic microorganism is selected from the genera *Lactobacillus, Streptococcus, Enterococcus*, another *bifidobacterium* and *Saccharomyces*.

77. The composition for use according to any one of paragraphs 58 to 76, wherein said composition is a medicament, a food product or a dietary supplement.

78. The composition for use according to any one of paragraphs 58 to 77, wherein the bacteria is formulated as a dietary supplement.

79. A method of reducing the risk of development and exacerbation of chronic respiratory diseases in a subject, said method comprising administering to and/or ingesting by said subject a composition derivable from a bifidobacteria (preferably *Bifidobacterium animalis*, more preferably from *Bifidobacterium animalis* subsp. *lactis*, more preferably *Bifidobacterium lactis* BL-04); preferably wherein said composition being derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably *Bifidobacterium animalis*, more preferably from *Bifidobacterium animalis* subsp. *lactis*, more preferably *Bifidobacterium lactis* BL-04) and/or a cell lysate of a bifidobacteria (preferably *Bifidobacterium animalis*, more preferably from *Bifidobacterium animalis* subsp. *lactis*, more preferably *Bifidobacterium lactis* BL-04).

80. The method of paragraph 79 wherein risk of development and exacerbation of chronic respiratory diseases is reduced due to modulation of the immune system by affecting viral action and/or viral effects; preferably wherein affecting viral action and/or viral effects include inhibiting virus replication and/or alleviation of inflammation caused by the virus infection.

81. The method according to paragraph 79 or 80 wherein said chronic respiratory diseases are asthma and/or COPD.

82. The method according to any one of paragraphs 79 to 81 wherein said virus is a rhinovirus, coronavirus, parainfluenza virus, adenovirus, enterovirus, or respiratory syncytial virus.

83. The method according to paragraph 82 wherein said virus is a rhinovirus, preferably a human rhinovirus (HRV).

84. The method according to any one of paragraphs 80 to 83, wherein modulation of the immune system modulates biomarker levels in the subject, preferably reduces biomarker levels in the subject.

85. The method according to paragraph 84 wherein said biomarkers are cytokines and/or chemokines.

86. The method according to any one of paragraphs 84 to 85 wherein said biomarkers are IL-8 and/or IL-1beta and/or MCP-1.

87. The method according to any one of paragraphs 80 to 86 wherein modulation of the immune system involves modulation of the innate immune system, the adaptive immune system or both.

88. The method according to any one of paragraphs 80 to 87 wherein modulation of the immune system increases the number of virus specific T-helper cells.

89. The method according to any one of paragraphs 80 to 88 wherein modulation of the immune system reduces levels of IL-8 and/or IL-1beta and/or MCP-1.

90. The method according to any one of paragraphs 79 to 89 wherein the subject is a human subject.

91. The method according to any one of paragraphs 79 to 90 wherein the subject is a human child.

92. The method according to any one of paragraphs 79 to 91 wherein alleviation of inflammation caused by virus infection causes alleviation of the symptoms of chronic respiratory diseases include one or more of the group consisting of: respiratory inflammation, throat soreness, sneezing, blocked nose, runny nose, a cough, coughing with chest congestion and coughing with wheezing.

93. The method according to any one of paragraphs 79 to 92, wherein the method is prophylactic.

94. The method according to any one of paragraphs 79 to 93, wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably *Bifidobacterium animalis*, more preferably from *Bifidobacterium animalis* subsp. *lactis*, more preferably *Bifidobacterium lactis* BL-04)/per day.

95. The method according to paragraph 94 wherein said composition is formulated at a dose of around or at $2\times10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

96. The method according to any one of paragraphs 79 to 95, comprising administering or ingesting at least one further probiotic microorganism.

97. The method according to paragraph 96, wherein the at least one further probiotic microorganism is selected from the genera *Lactobacillus, Streptococcus, Enterococcus*, another *bifidobacterium* and *Saccharomyces*.

98. The method according to any one of paragraphs 79 to 97, wherein the composition is formulated a medicament, a food product or a dietary supplement.

99. The method according to any one of paragraphs 79 to 98, wherein the composition is formulated as a dietary supplement.

100. Use of a composition derivable from a bifidobacteria (preferably *Bifidobacterium animalis*, more preferably from *Bifidobacterium animalis* subsp. *lactis*, more preferably *Bifidobacterium lactis* BL-04) in the manufacture of a composition for reducing the risk of development and exacerbation of chronic respiratory diseases in a subject; preferably wherein said composition being derivable from a bifidobacteria (preferably *Bifidobacterium animalis*, more preferably from *Bifidobacterium animalis* subsp. *lactis*, more preferably *Bifidobacterium lactis* BL-04) is a composition comprising a bifidobacteria (preferably *Bifidobacterium animalis*, more preferably from *Bifidobacterium animalis* subsp. *lactis*, more preferably *Bifidobacterium lactis* BL-04) and/or a fermentation product of a bifidobacteria (preferably *Bifidobacterium animalis*, more preferably from *Bifidobacterium animalis* subsp. *lactis*, more preferably *Bifidobacterium lactis* BL-04) and/or a cell lysate of a bifidobacteria (preferably *Bifidobacterium animalis*, more preferably from *Bifidobacterium animalis* subsp. *lactis*, more preferably *Bifidobacterium lactis* BL-04).

101. The use of paragraph 100, wherein risk of development and exacerbation of chronic respiratory diseases, is reduced due to modulation of the immune system by affecting viral action and/or viral effects; preferably wherein affecting viral action and/or viral effects include inhibiting virus replication and/or alleviation of inflammation caused by the virus infection.

102. The use according to paragraph 100 or 101 wherein said chronic respiratory diseases are asthma and/or COPD.

103. The use according to any one of paragraphs 100 to 102 wherein said virus is a rhinovirus, coronavirus, parainfluenza virus, adenovirus, enterovirus, or respiratory syncytial virus.

104. The use according to paragraph 103 wherein said virus is a rhinovirus, preferably a human rhinovirus (HRV).

105. The use according to any one of paragraphs 101 to 104, wherein modulation of the immune system modulates biomarker levels in the subject, preferably reduces biomarker levels in the subject.

106. The use according to paragraph 105 wherein said biomarkers are cytokines and/or chemokines.

107. The use according to any one of paragraphs 105 to 106 wherein said biomarkers are IL-8 and/or IL-1beta and/or MCP-1.

108. The use according to any one of paragraphs 101 to 107 wherein modulation of the immune system involves modulation of the innate immune system, the adaptive immune system or both.

109. The use according to any one of paragraphs 101 to 108 wherein modulation of the immune system increases the number of virus specific T-helper cells.

110. The use according to any one of paragraphs 101 to 109 wherein modulation of the immune system reduces levels of IL-8 and/or IL-1beta and/or MCP-1.

111. The use according to any one of paragraphs 100 to 110 wherein the subject is a human subject.

112. The use according to any one of paragraphs 100 to 111 wherein the subject is a human child.

113. The use according to any one of paragraphs 100 to 112 wherein alleviation of inflammation causes by virus infection causes the alleviation of the symptoms of chronic respiratory diseases, including one or more of the group consisting of: respiratory inflammation, throat soreness, sneezing, blocked nose, runny nose, a cough, coughing with chest congestion and coughing with wheezing.

114. The use according to any one of paragraphs 100 to 113, wherein the use is prophylactic.

115. The use according to any one of paragraphs 100 to 114, wherein the composition derivable from a bifidobacteria (preferably *Bifidobacterium animalis*, more preferably from *Bifidobacterium animalis* subsp. *lactis*, more preferably *Bifidobacterium lactis* BL-04) is formulated at a dose of $10^8$ to $10^{12}$ CFU of a bifidobacteria (preferably a bifidobacteria (preferably *Bifidobacterium animalis*, more preferably from *Bifidobacterium animalis* subsp. *lactis*, more preferably *Bifidobacterium lactis* BL-04)/per day.

116. The use according to paragraph 115 wherein said composition is formulated at a dose of around or at $2 \times 10^9$ CFU of a bifidobacteria (preferably *Bifidobacterium animalis*, more preferably from *Bifidobacterium animalis* subsp. *lactis*, more preferably *Bifidobacterium lactis* BL-04)/per day.

117. The use according to any one of paragraphs 100 to 116, wherein the composition comprises at least one further probiotic microorganism.

118. The use according to paragraph 117, wherein the at least one further probiotic microorganism is selected from the genera *Lactobacillus, Streptococcus, Enterococcus*, another *bifidobacterium* and *Saccharomyces*.

119. The use according to any one of paragraphs 100 to 118, wherein said composition is a medicament, a food product or a dietary supplement.

120. The use according to any one of paragraphs 100 to 119, wherein the bacteria is formulated as a dietary supplement.

121. A composition or a method or a use wherein said composition also comprises or consists of one or more of an anti-microbial agent, a stabilising agents, a dye and a drying agent.

122. A method, use or composition as generally taught herein with reference to the Examples and Figures.

FIGURES

Figure 3:
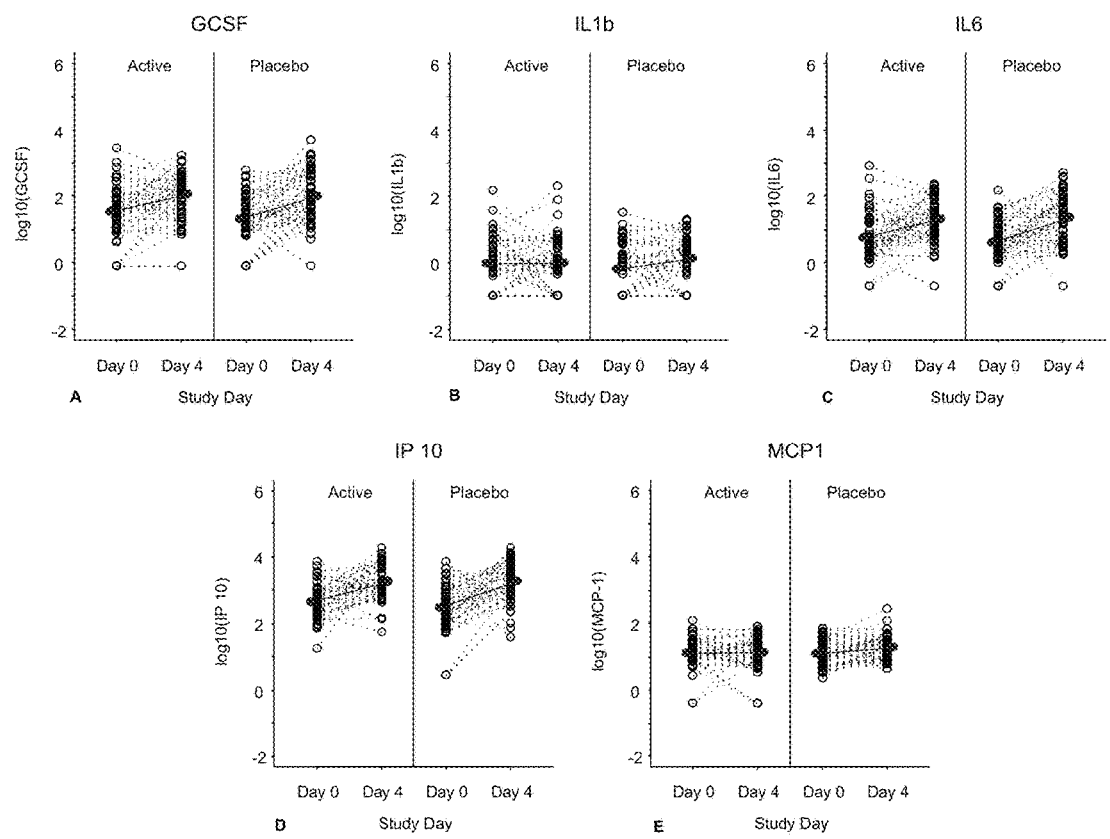

FIG. 3 shows a graphical representation of Nasal Wash Cytokine Analyses. Day 0 and day 4 cytokine response for G-CSF (A), IL-1beta (B), IL-6 (C), IP-10 (D), and MCP-1 (E). Red lines (solid lines) identify the mean trajectory for the day 0 to day 4 cytokine response.

Figure 4:
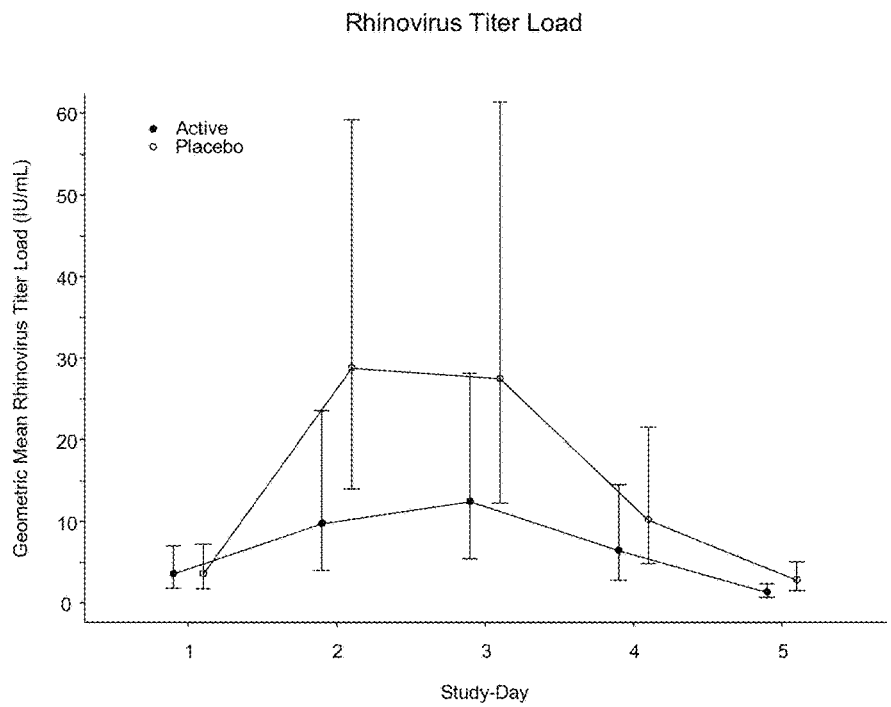

FIG. 4 shows a graphical representation of Rhinovirus titer load on study days 1, 2, 3, 4, and 5. Circles identify the geometric mean rhinovirus viral load estimate, and vertical lines identify the 95% confidence interval.

Figure 5:
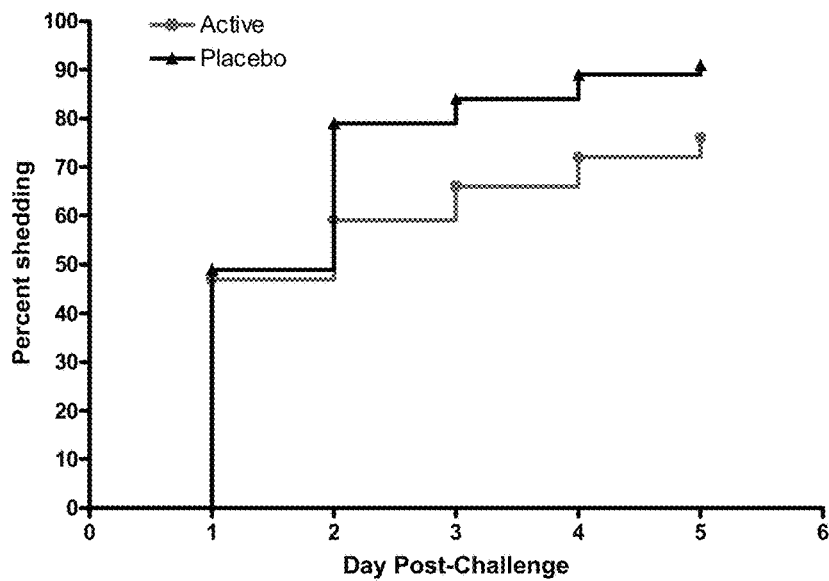

FIG. 5 shows a graphical representation of time to virus shedding. The line marked with -○- is the probiotic group and the line above that marked with -Δ- is the placebo group.

Figure 6:
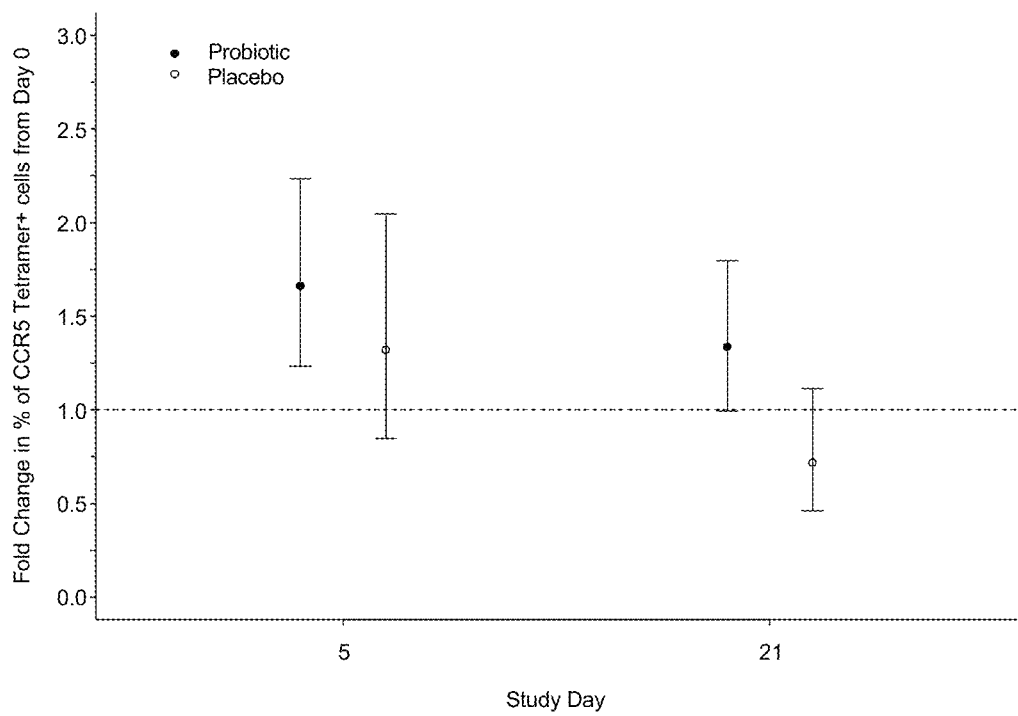

FIG. 6 shows the fold change in HRV39-specific CCR5+ T-helper cells.

Figure 7:
Figure 7:
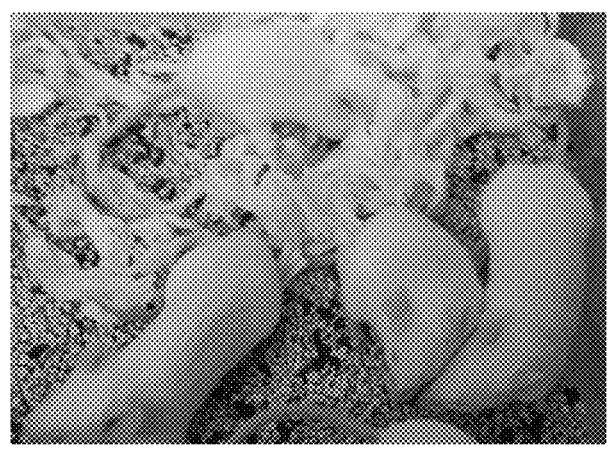

FIG. 7 shows phenotype of mice (control group vs probiotic group) at day 56

Figure 8:
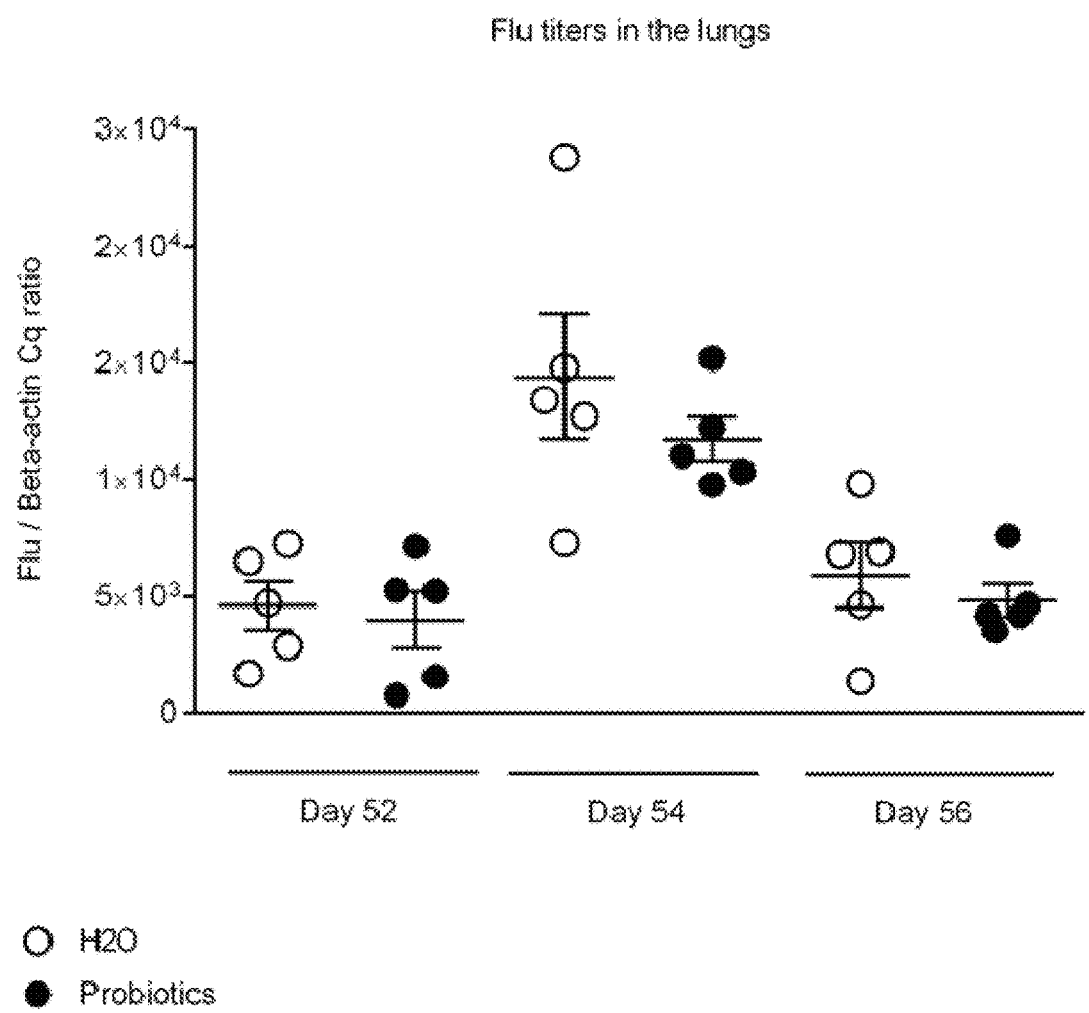

FIG. 8 shows Flu titers in the lungs of mice (control group vs probiotic group)

Figure 9:
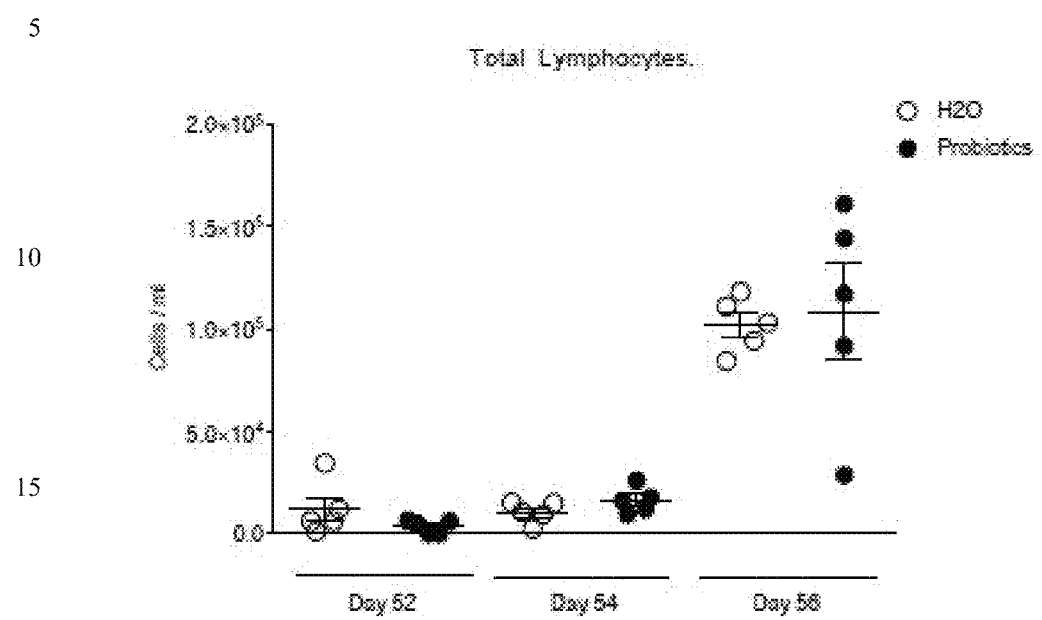
Figure 9:
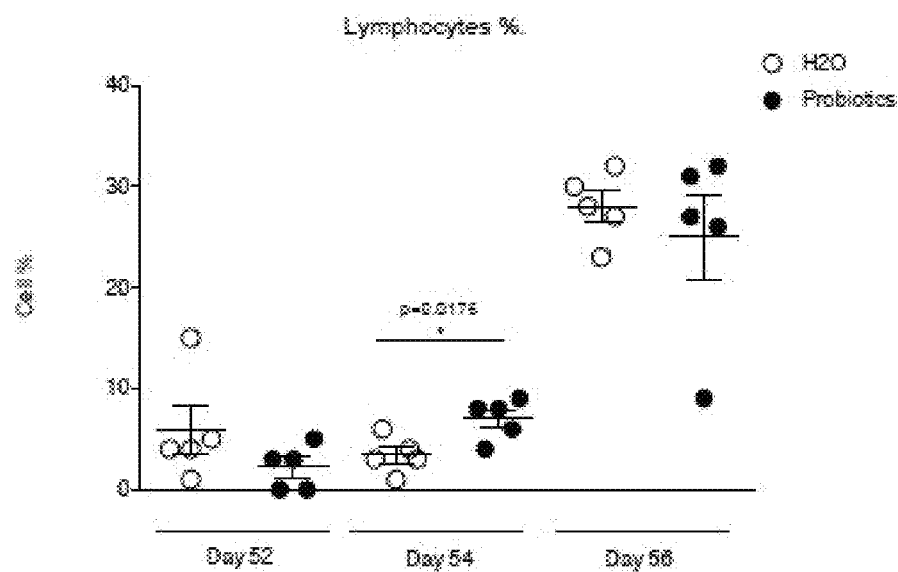

FIG. 9 shows lymphocyte count and proportion in Bronchoalveolar lavage fluid ("BALF")

Figure 10:
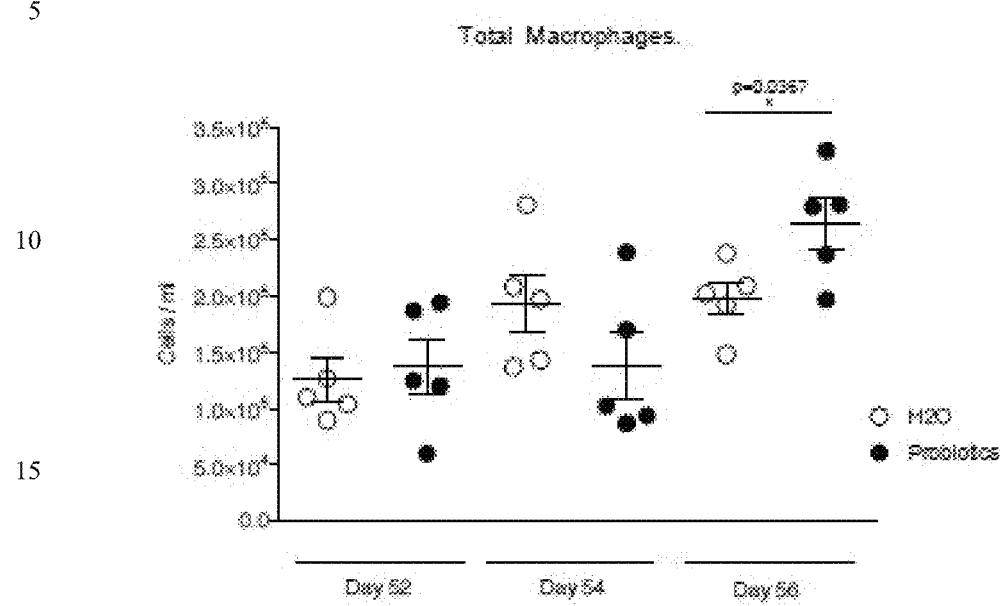
Figure 10:
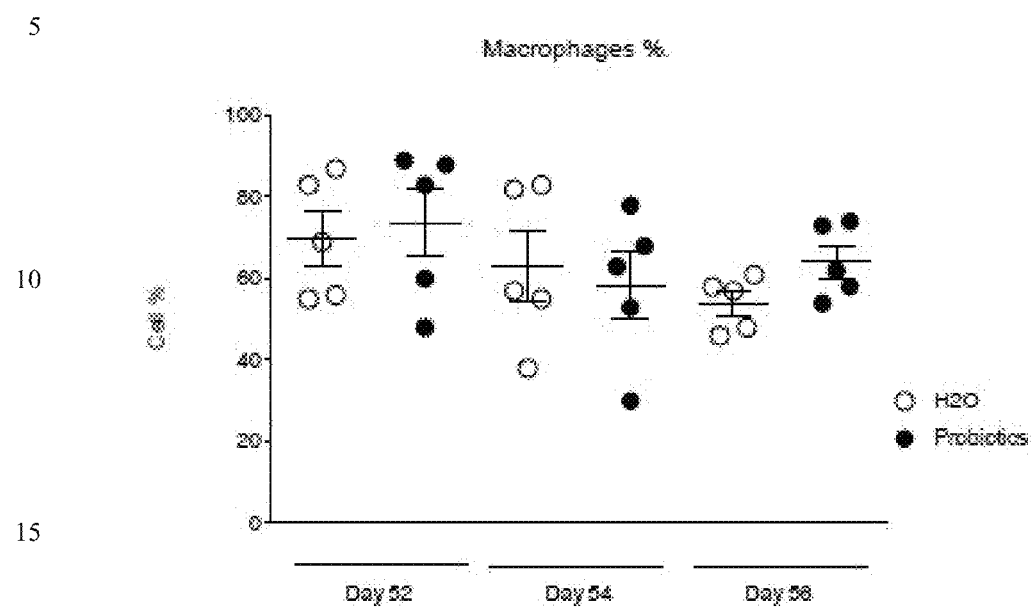

FIG. 10 shows macrophage count and proportion in BALF

EXAMPLES

The present invention will be further described with reference to the following Examples Example 1—Use of BL-04 in Healthy Adults Study Design and Flow Healthy adult volunteers were selected according to clinical study protocol to participate into the randomized, double-blind, placebo controlled study. Probiotic Bl-04 or placebo was administered for 28 days before inoculating the human rhinovirus (HRV) intranasally. The nasal lavages were taken daily up to 5 days post-infections to analyze the viral load and the inflammatory marker IL-8.

This study was a randomized, double-blinded, placebo-controlled trial to assess the effects of an orally ingested probiotic on the host response to an experimental rhinovirus infection. The virus challenge day was Study Day 0. Healthy, young adult volunteers were started on Bl-04 or placebo on Study Day −28 after baseline blood and nasal lavage specimens had been collected. Subjects were instructed to consume one sachet of study product each day and were seen in the study center on study days −21, −14 and −7 to re-supply the study product and to assure compliance. The consumption of the study product was continued through Study Day 5.

On Study Day 0, prior to virus inoculation, blood and nasal lavage was collected for study assays. The volunteers were then seen daily for the next 5 days to record symptoms and adverse events and to collect nasal lavage for viral culture.

On study day 0, 5 and 21 blood was collected to analyse the adaptive immune cells by flow cytometry.

Figure 1:
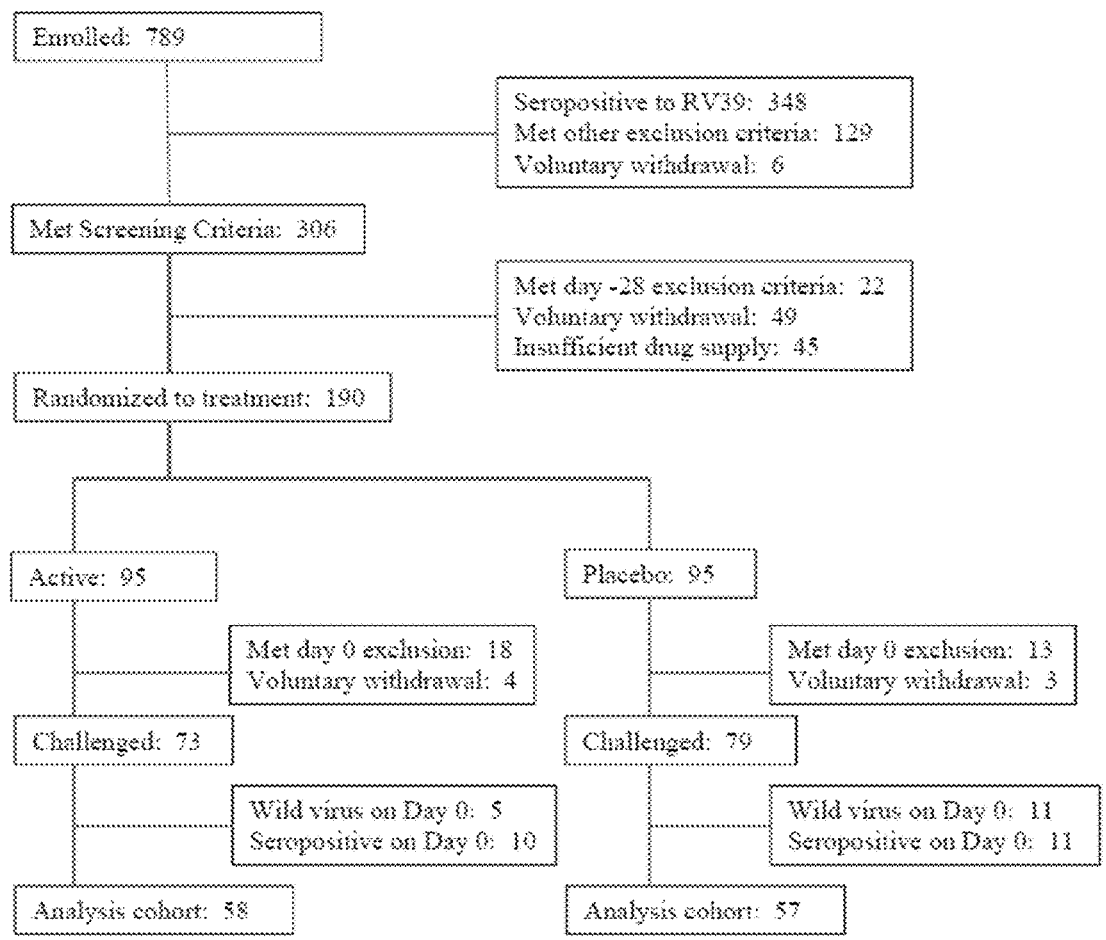
FIG. 1 shows a Flow Chart detailing the flow of subjects through the study of Example 1.

Subjects:

Seven hundred eighty-nine (789) subjects signed consent for participation in the trial. The study was conducted in three cohorts two in the spring of 2013 and one in the fall of 2013. The flow of subjects through the study is shown in FIG. 1.

One-hundred ninety (190) subjects were randomized to treatment and, after withdrawals and per protocol exclusions, 115, 58 in the active group and 57 in the placebo group, were available for analysis. The planned analysis sample size for the study was 120. The pivotal analysis for the study was done, as described in the statistical plan, on those subjects who were infected with rhinovirus, 51 subjects in the active group and 55 subjects in the placebo group. We note that there were a large number of exclusions form the study due to the consumption of prohibited foods (for example other probiotics) and voluntary withdrawal (See FIG. 1).

The study population was drawn primarily from the UVa student population and the demographics of the study reflect that population. The study arms were appropriately balanced for the demographics measured. Details of the demographics of a study subjects are given in table 1 below.

TABLE 1

Study demographics.

| | Active (N = 58) | Placebo (N = 57) | P value |
|---|---|---|---|
| Gender | | | |
| Male | 19 (33%) | 24 (42%) | 0.339 |
| Female | 39 (67%) | 33 (57%) | |
| Race | | | |
| Asian | 2 (3%) | 8 (14%) | 0.270 |
| Black | 3 (5%) | 2 (4%) | |
| White | 52 (90%) | 46 (81%) | |
| Other | 1 (2%) | 1 (2%) | |
| Ethnicity | | | |
| Hispanic | 3 (5%) | 4 (7%) | 0.857 |
| Non-hispanic | 54 (93%) | 52 (91%) | |
| Unknown | 1 (2%) | 1 (2%) | |
| Age (yrs, mean (SD)) | 22 (6) | 23 (7) | 0.975 |

The effectiveness of the blinding of subjects to study treatment was assessed after the volunteers had consumed the study treatment for 28 days and before they were challenged with virus (see Table 2 below). The majority of volunteers in both treatment groups believed they were taking the placebo preparation but there was no evidence of unblinding (Likelihood Ratio Chi-square Test: P=0.56).

TABLE 2

The assessment of blinding.

| | Subject Guess | | |
|---|---|---|---|
| Actual Group | Active | Placebo | Don't know |
| Active (N (%)) | 11 (19.0) | 31 (53.4) | 16 (27.6) |
| Placebo (N (%)) | 7 (12.3) | 31 (54.4) | 19 (33.3) |

There were no serious adverse events during the study.

Results

The overall purpose of this study was to address the hypothesis that prophylaxis of human volunteers with probiotic bifidobacteria, preferably *Bifidobacterium animalis*, more preferably from *Bifidobacterium animalis* subsp. *lactis*, more preferably *Bifidobacterium lactis* BL-04 will inhibit virus-induced innate inflammatory responses characterized for example by IL-8, while enhancing the adaptive host response, for example antibody production. The study addressed the following specific outcome measures:

Primary End-Point of the Clinical Study

Figure 2:
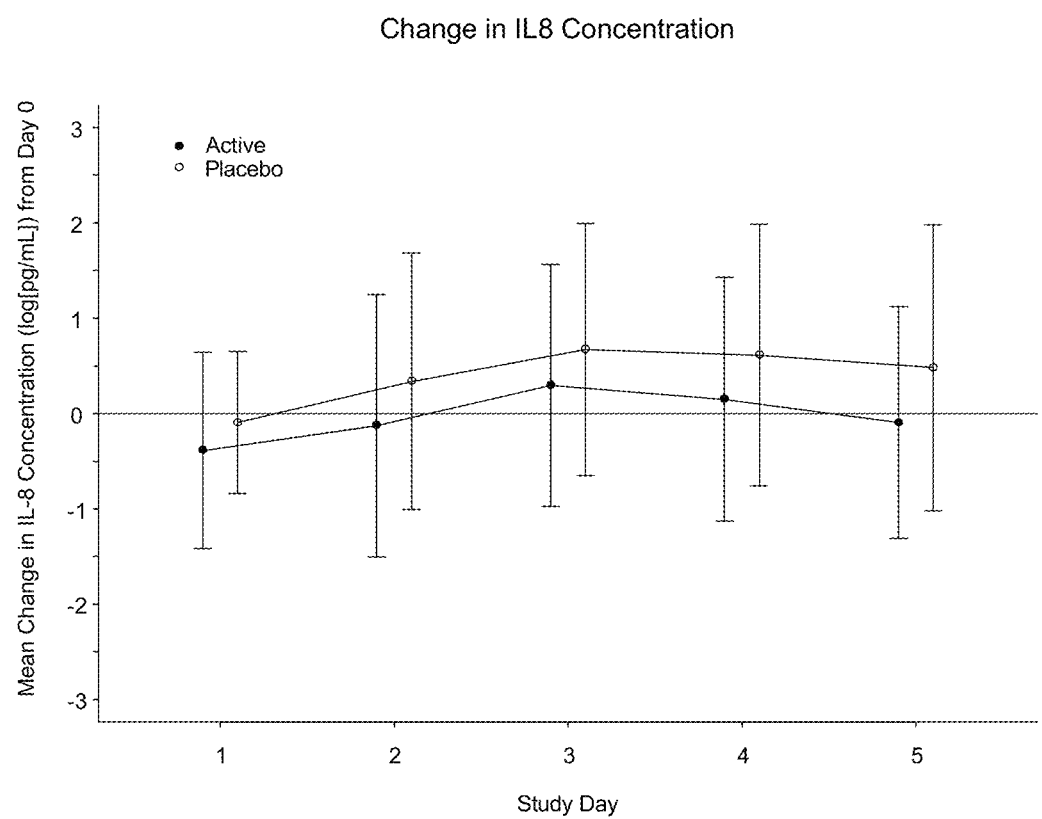
FIG. 2 shows a graphical representation of the analysis of nasal wash for IL8 levels in the rhinovirus infected subset of subjects only.

1) Inflammatory Response in Nasal Mucosa as Characterized by IL-8 Levels in Nasal Lavages Nasal lavage IL-8 concentration was assessed by comparing the change from the baseline value in the concentration at 72 hours of observation (72 hr. measurements minus the 0 hr. measurement). The increase in IL-8 concentration between study day 0 and study day 3 was not significantly different between the probiotic and placebo groups (geometric mean ratio, active:placebo for change in concentration at day 3=0.69, p=0.14) (Table 3 line Day 3; FIG. 2). There was, however, a significant difference in the change in IL-8 in response to virus infection over the course of the 5 days after virus challenge (geometric mean ratio (A:P)=0.65, p=0.03 (Table 3 line Day overall; FIG. 2), indicating that the overall inflammation was less in probiotic group during the infection. The IL-8 concentrations were not any different at day −28 when the study treatment was started. However, on day 0 prior to challenge, the IL-8 concentrations in the lavage from placebo-treated volunteers were significantly decreased from day −28 and were significantly lower than in the active-treatment group (Table 4). The concentration of IL-8 in nasal lavage increased following virus infection but these increases were not statistically significant in the active treatment group. The increase in IL-8 concentration was statistically significant in the placebo group on study days 3, 4 and 5 (Table 5; FIG. 1).

TABLE 5

Unadjusted estimates for the change in IL-8 concentration during infection (days 1-5) from day 0 (i.e. baseline) when expressed as a ratio of geometric means.

| Study Group | Ratio | Estimated Geometric Mean Ratio | Lower 95% CL | Upper 95% CL | Pvalue Ho: Ratio = 1 |
|---|---|---|---|---|---|
| Active | Day 1: Day 0 | 0.68 | 0.53 | 0.87 | 0.003 |
| Placebo | | 0.91 | 0.72 | 1.15 | 0.432 |
| Active | Day 2: Day 0 | 0.88 | 0.60 | 1.29 | 0.507 |
| Placebo | | 1.40 | 0.97 | 2.02 | 0.069 |
| Active | Day 3: Day 0 | 1.34 | 0.94 | 1.93 | 0.108 |
| Placebo | | 1.96 | 1.38 | 2.77 | <0.001 |
| Active | Day 4: Day 0 | 1.16 | 0.80 | 1.68 | 0.417 |
| Placebo | | 1.85 | 1.30 | 2.63 | 0.001 |
| Active | Day 5: Day 0 | 0.91 | 0.62 | 1.33 | 0.622 |
| Placebo | | 1.62 | 1.12 | 2.33 | 0.011 |

TABLE 3

Baseline (day −28) adjusted between-group comparisons of the change in IL-8 concentration during infection from day 0, when expressed as a ratio of geometric means.

| Day | Ratio | Estimated Ratio of Geometric Means | Lower 95% CL | Upper 95% CL | Un-adjusted Pvalue | Bonferroni Lower 95% CL | Bonferroni Upper 95% CL | Bonferroni Corrected Pvalue |
|---|---|---|---|---|---|---|---|---|
| 1 | A:P | 0.75 | 0.53 | 1.05 | 0.096 | 0.48 | 1.16 | 0.385 |
| 2 | A:P | 0.63 | 0.37 | 1.06 | 0.083 | 0.32 | 1.24 | 0.334 |
| 3 | A:P | 0.69 | 0.42 | 1.13 | 0.141 | | | |
| 4 | A:P | 0.63 | 0.38 | 1.05 | 0.077 | 0.33 | 1.22 | 0.308 |
| 5 | A:P | 0.56 | 0.33 | 0.96 | 0.034 | 0.29 | 1.11 | 0.135 |
| Overall | A:P | 0.65 | 0.44 | 0.95 | 0.026 | | | |

TABLE 4

Summary for the analysis of day 0 IL-8 concentration (loge[pg/mL]), after 28 days of probiotic supplementation.

| Study Arm | Estimate Geometric Mean IL-8 Concentration | Lower 95% Confidence Limit | Upper 95% Confidence Limit |
|---|---|---|---|
| Active | 97.2 | 68.5 | 137.9 |
| Placebo | 58.0 | 43.4 | 77.5 |

| Parameter Comparison | Study Arm Ratio | Estimated Geometric Mean Ratio | Lower 95% CL | Upper 95% CL | Pvalue Ho: Ratio = 1 |
|---|---|---|---|---|---|
| Geometric Mean | Active: Placebo | 1.68 | 1.07 | 2.62 | 0.025 |

Secondary End-Points
1, Biomarker Response of Nasal Mucosa

Biomarker (cytokine and chemokine) profiles were measured from nasal lavages using multiplex ELISA assays. The following biomarkers were analyzed on days −28, 0, 1, 2, and 4 in relation to the virus challenge: TGF-beta1, G-CSF, GM-CSF, IFN-gamma, IL-1alpha, IL-12p70, IL-15, MIP-3alpha, IL-1beta, IL-6, IL-10, IP-10, MCP-1, MIP-1alpha, RANTES, and TNF-alpha (trimer). The concentrations of many of these analytes were too low to permit a valid analysis. The results for G-CSF, MIP-3alpha, IL-1beta, IL-6, IP-10, and MCP-1 were considered valid for analysis. Innate inflammatory markers were noted to increase after infection as expected. There were no significant differences between the treatment groups. However, there was a trend for a higher IL-1beta (p=0.071) and MCP-1 (p=0.075) response in the nasal lavages for a placebo group when a change in response from day 0 (infection) to day 4 was analyzed (FIG. 3; Table 6). This result supports the IL-8 results because IL-1beta and MCP-1 are both inflammatory cytokines. Therefore it can be seen that inflammation is reduced.

TABLE 6

| Cytokine | Active Day 0 GM [95% CI] | Placebo Day 0 GM [95% CI] | Pvalue Active vs. Placebo | Active GM Ratio (Day 4: Day 0) | Active GM Ratio (Day 4:Day 0) Pvalue | Placebo GM Ratio (Day 4: Day 0) | Placebo GM Ratio (Day 4: Day 0) Pvalue | Active vs. Placebo (Day 4: Day 0) Pvalue |
|---|---|---|---|---|---|---|---|---|
| G-CSF | 33.4 [20.1, 55.4] | 20.4 [12.7, 32.6] | 0.155 | 3.35 [1.95, 5.73] | <0.001 | 4.87 [2.78, 8.54] | <0.001 | 0.336 |
| IL-1beta | 0.9 [0.6, 1.5] | 0.6 [0.4, 1.0] | 0.250 | 1.04 [0.54, 1.85] | 0.889 | 2.13 [1.24, 3.69] | 0.007 | 0.071 |
| IL-6 | 5.5 [3.5, 8.6] | 3.9 [2.6, 5.9] | 0.283 | 3.73 [2.12, 6.57] | <0.001 | 5.56 [3.08, 10.05] | <0.001 | 0.331 |
| IP-10 | 439.1 [317.0, 608.3] | 298.8 [198.2, 450.6] | 0.144 | 4.10 [2.57, 6.53] | <0.001 | 6.24 [3.66, 10.62] | <0.001 | 0.236 |
| MCP-1 | 12.9 [9.8, 17.0] | 12.2 [9.5, 15.6] | 0.757 | 1.02 [0.71, 1.48] | 0.878 | 1.55 [1.18, 2.02] | 0.002 | 0.075 |

2. Rhinovirus Replication

Rhinovirus quantity was measured in nasal lavage by standard culturing methods. Nasal lavage viral titers were generally greater in the placebo-treated than in the probiotic-treated subjects, however, this difference was not statistically significant (p=0.1) (Table 7, FIG. 4). If an assumption on anti-viral efficacy of Bl-04 is done and Intention-to-Treat population is used that includes those who did not get a clinical cold although HRV was inoculated there is a statistical less rhinovirus in nasal lavages of the subjects in probiotic group (p=0.026)(Table 8). Using log-rank test, a post-hoc analysis (without Bonferroni correction) found that the time to virus shedding was longer (p=0.02)(FIG. 5) and the proportion of subjects with virus shedding was lower (p=0.04) in the probiotic treated group (FIG. 5). Thus, the rhinovirus replication is impaired in the probiotic-treated subjects.

TABLE 7

| Source of Variation | Degrees of Freedom | Wald Chi-square Statistics | Pvalue |
|---|---|---|---|
| Study-Arm | 1 | 2.68 | 0.101 |
| Study-Day | 4 | 97.37 | <0.001 |
| Study-Arm × Study Day | 4 | 7.44 | 0.114 |

TABLE 8

| Source of Variation | Degrees of Freedom | Wald Chi-square Statistics | Pvalue |
|---|---|---|---|
| Study-Arm | 1 | 4.92 | 0.026 |
| Study-Day | 4 | 93.01 | 0.000 |
| Study-Arm × Study Day | 4 | 8.95 | 0.062 |

The number of circulating RV-specific T-cells in the subset of DR4+ subjects: Two HRV39 peptide/MHC II tetramers will be used for direct ex vivo quantitative analysis of circulating HRV39-specific CD4+ T cell frequencies using PBMC specimens. It was found that fold change in HRV39-specific CCR5+T-helper cells was greater in probiotic group at day 21 (p=0.042) (FIG. 6).

The results for FIG. 6 are as follows:

| Day | Ratio | Fold Change | Lower 95% CL | Upper 95% CL | Unadjusted P Value | Bonferroni Lower 95% CL | Bonferroni Upper 95% CL | Bonferroni Corrected P Value |
|---|---|---|---|---|---|---|---|---|
| 5 | Probiotic: Placebo | 1.24 | 0.75 | 2.06 | 0.390 | 0.69 | 2.23 | 0.780 |
| 21 | | 1.84 | 1.11 | 3.05 | 0.021 | 1.02 | 3.31 | 0.042 |

The results indicate that adaptive immune response against HRV39 was improved after the infection and Bl-04 supplementation could thus provide benefit against reinfections of HRVs.

The results of Example 1 show that the prophylactic use of Bl-04 in an experimental rhinovirus infection model decreased the inflammatory IL-8 cytokine levels in nasal lavage. The reduced inflammatory response in HRV infection by Bl-04 was supported by the trend for higher induction of inflammatory cytokines IL-1beta and MCP-1 in placebo group, but not in the probiotic group. These results indicate that consumption of Bl-04 may alleviate the inflammatory response in the airways. In addition, the results above show that Bl-04 consumption is effective against HRV replication in healthy subjects. This also indicates that Bl-04 could prevent asthma development in infants and/or children and be beneficial in preventing asthma and COPD exacerbations that are associated with rhinovirus infections.

Example 2—Chronic Respiratory Diseases

Introduction

The above study demonstrates that probiotic *B. lactis* Bl-04 decreases rhinovirus shedding and IL-8 levels during HRV infection in humans indicating an anti-viral and anti-inflammatory effect, respectively, by the probiotic.

Without wishing to be bound by theory, we believe that the administration of Bl-04 could decrease risk (anti-viral effect) or severity (anti-inflammatory effect) of asthma or COPD exacerbations. To test this, mouse model that has been made susceptible for human rhinoviruses (Bartlett et al. 2008) is used to test the efficacy of Bl-04 supplementation against asthma or COPD exacerbations.

Asthma is studied in mice that are sensitized to ovalbumin, a model allergen, and COPD is studied in mice that are exposed chronically to cigarette smoke (Stevenson and Birrell 2011). Optionally probiotic Bl-04 is administered prophylactically in experimental rhinovirus challenge model using asthmatic or COPD human subjects that have mild and stable disease (Del Vecchio et al. 2015; Contoli et al. 2007; Cheung et al. 1995).

Animal Studies

Animal Model for HRV Infection

The effect of the Bl-04 supplementation against rhinovirus is studied in mice by using minor group rhinovirus infected mice or mice transgenic for human ICAM-1 receptor that acts as a natural receptor for human major group rhinoviruses in humans (e.g. Bartlett 2008 Nat Med). This model is used to study the effect Bl-04 against HRV infection. When combined with other specific models, explained below, (i) reduction of asthma development risk, (ii) reduction of asthma exacerbation risk, and for (iii) reduction of COPD exacerbation risk may be studied.

Dosing of Probiotic in Animal Experiments

Bl-04 is preferably fed at dose of $2*10^9$ CFU/day for 2 weeks, before HRV infection. The probiotic is administered either by gavage or mixed into small amount of feed or liquid to assure that the dose is ingested.

The Effect of the Probiotic Bl-04 on Asthma Development

The HRV susceptible mice are administered Bl-04 or placebo for 1 week before exposing them to HRV, RSV, or placebo infection at day 7 post-natal (Schneider 2012). The challenge is done at 50% infective dose. Rationale for RSV inclusion is that Bl-04 could be potentially effective against other asthma predisposing viruses than HRV as well (Schwarze et al. 1997). RSV causes wheezing more commonly then HRV. We monitor the inflammation of the airways and virus titers in mice during the infection. Bl-04 has antagonistic effects on HRV and IL-8 levels.

After the HRV infection, the mice are further sensitized to model antigen ovalbumin (OVA) that can be used to induce asthma like symptoms in airways by three consecutive doses using alum as an adjuvant. The inflammation of the airways and development of airway hyper-responsiveness are monitored by standard histological and molecular methods. The early life or post-natal, Bl-04 supplementation and decrease in HRV pathology and inflammation during infection decrease inflammation and asthma pathology in adult mice later in their life.

The Effect of the Probiotic Bl-04 on Asthma Exacerbations

The HRV susceptible mice are sensitized to ovalbumin with alum adjuvant or PBS as a control. OVA is administered on three consecutive days to induce airway inflammation. The supplementation of the HRV susceptible mice is started with Bl-04 or placebo as described above. After 2 weeks of Bl-04 supplementation, a HRV challenge at 50% infective dose is given to mice and inflammation (e.g. IL-8) of the airways and rhinovirus titers in the airway lavages are analyzed from mice. Furthermore, airway pathology is monitored histologically. In the Bl-04 group the inflammation, HRV titer, and pathology are alleviated and potentially the infectivity of HRV is decreased.

The Effect of the Probiotic Bl-04 on COPD Exacerbations

The HRV susceptible mice are exposed to cigarette smoke for at least 1 month (or not in the case of the placebo group), to induce immunological and pathological changes observed in COPD (Stevenson 2007). The supplementation of the mice with Bl-04 or placebo is initiated for 2 weeks after chronic COPD like changes have occurred. Then the mice are inoculated with 50% infective dose of HRV to induce acute virus induced exacerbation. Inflammation (incl. IL-8), HRV titers and lung pathology are analyzed. In the Bl-04 group, the inflammation, HRV titer, and pathology are alleviated and potentially the infectivity of HRV is decreased.

Example 3—Effect of Bl-04 on Asthma Exacerbation

Study Design
Treatment Groups:
1. Negative control group. Treatment with vehicle ($H_2O$).
2. Treatment with Bl-04.
Number of mice per group=15.
House-Dust-Mite (HDM) Induced Asthma Exacerbation:
Day 0-28: Three times per week administration of HDM in 30 ul PBS per nasal.
Day 28-49: Daily administration of Bl-04 or vehicle ($H_2O$) by cereal treat.
Day 49: Administration of sub-lethal dose of influenza virus (PR8) per nasal.
Day 52: 5 animals per group are sacrificed for analysis.
Day 54: 5 animals per group are sacrificed for analysis.
Day 56: 5 animals per group are sacrificed for analysis.

8 week old BALB/c mice were used for the study. Potable water and food were available ad libitum.

At days 0 to 28, animals were administered three times per week with 15 µg of HDM in a volume of 30 µl PBS per nasal. Mice were anesthetized by intraperitoneal injection with 9.75 mg Xylasol and 48.75 mg Ketasol per kg and administered with 15 µg of HDM in a volume of 30 µl PBS per nasal.

At days 28 to 49, animals were administered with vehicle (water, Group 1) or Bl-04 (Group 2) by oral gavage ($1\times10^9$ CFU/day) and by cereal treat ($1\times10^9$ CFU/day/cereal.

200 μl of water or Bl-04, reconstituted in water at a concentration of $5\times10^9$ CFU/ml, was placed on a single flake of cereal ('Special K' manufactured by Kellogg's). The probiotic treatments were prepared fresh each day of administration. One flake of cereal per mouse in each cage was placed on a feeding tray inside the cage and the mice were able to eat during the day.

On the same day, 200 μl of water or the reconstituted probiotic was administered to mice by oral gavage.

On day 49, mice were inoculated with a sub-lethal dose of influenza A virus (250 PFU per nasal; influenza strain H1N1 PR/8/34)). The virus material was stored at −75° C.±10° C. and was defrosted prior to administration. Once defrosted, the material was diluted in cold PBS (4° C.) corresponding to 250 PFU/50 μl for A/PR/8/34. The diluted virus was kept on ice until administration to the mice.

The animals were anaesthetized by intraperitoneal injection with 9.75 mg Xylasol and 48.75 mg Ketasol per kg body weight and each animal received 50 μl virus solution by intranasal inoculation.

On days 52, 54 and 56 five animals per group were sacrificed by lethal intraperitoneal injection with pentabarbitol immediately followed by a bronchoalveolar lavage (BAL) in 500 ul of saline and tissue isolation (lung).

Cells were isolated from the BAL fluid and differential cell counts performed (200 cell counts/samples). The total cell numbers in the bronchoalveolar lavage (BAL) fluid was determined using a Coulter Counter (IG Instrumenten-Gesellschaft AG, Basel, Switzerland). Differential cell counts were performed (200 cell counts/samples) based upon standard morphological and cytochemical criteria on cytospins stained with Diff-Quik solution (Dade Behring, Siemens Healthcare Diagnostics, Deerfield, Ill.).

Lung lobes were isolated for the quantification of viral load in lung tissue by quantitative PCR. Lung lobes were carefully isolated and placed in 2 ml Eppendorf tubes containing 1 ml of TRI-Reagent (Molecular Research Centre Inc. Catalogue number: TR 118) and snap frozen in dry ice. Samples were then stored at −80° C. until processing.

Lung lobes preserved in TRI-Reagent, were slowly thawed at room temperature. Sterile, stainless steel beads (Qiagen. Catalogue Number: 69989) were placed in each sample tube and lungs were homogenised using a TissueLyser (Qiagen. Catalogue Number: 85220), at a frequency of 25 Hz for 3 minutes.

RNA extraction using TRI-Reagent (Molecular Research Centre Inc. Catalogue number: TR 118) was completed following manufacturer's instructions (http://mrcgene.com/wp-content/uploads/2014/06/TRIMay2014.pdf).

RNA concentration in each sample was measured using a Thermo Scientific NanoDrop™ 1000 Spectrophotometer (Thermo Fisher Scientific). RNA was treated with DNase (Invitrogen) to avoid genomic DNA contamination before RNA was converted to cDNA by reverse transcription and cDNA was quantified by real-time PCR. Samples were normalized with reference to β-actin expression levels.

Samples were amplified in a one-step RT-PCR at a final reaction volume of 10 μl, containing 5 μl of iTaq universal SYBR Green reaction mix (BIO-RAD Laboratories, Catalogue number 172-5150), 0.125 μl of iScript reverse transcriptase (BIO-RAD. Catalogue number: 172-5150), 0.5 μl of Influenza PR8 Matrix protein forward and reverse primers (5_-GGACTGCAGCGTAGACGCTT-3_ and 5_-CATCCT-GTATATGAGGCCCAT-3) or Beta actin (5_-GAT-CAAGATCATTGCTCCTCCTGA-3_ and 5_-CAGCTCA-GTAACAGTCCGCC-3_), 0.375 μl of RNAse free water (BIO-RAD. Catalogue number: 172-5150), and 4 μl of RNA at 125 ng/μl.

Thermo-cycling was performed in a CFX-96 real-time PCR system (BIO-RAD) using the following protocol: Reverse transcription reaction: 10 min at 50° C., then polymerase activation and DNA denaturation: 1 min at 95° C., then denaturation: 95° C. for 10 sec, then annealing/extension+ plate read: 30 sec at 60° C., for total of 40 cycles.

Graphs and Statistical Analysis.

Statistics were performed as either an unpaired t-test (quantification of viral titer in lung tissue) or as one-way ANOVA. Error bars in the figures represent Standard Error of the Mean (SEM).

Results

The administration of the probiotic was well tolerated by the mice. The mice received the probiotic by gavage, which ensured all mice were exposed to the bacteria, and additionally cereal in the cage was soaked with the probiotic and rapidly eaten by the mice each day. No substantial variation was noted within groups that would indicate that some mice consumed more of the bacteria-soaked cereal than other mice.

Treating the mice with HDM introduced asthma-like conditions in the mice. After treatment with probiotics or vehicle the mice were infected with influence virus. The appearance of the probiotic treated mice was strikingly different, with the probiotic mice appearing to have less morbidity. This observation suggests that the probiotic treated mice might have been protected against the initial allergic asthma response, and/or the probiotic bacteria protect against morbidity (and potentially mortality) during viral infection. Thus, the overall well-being of the mice seems to be increased (FIG. 7). This is also illustrated by the tendency of the viral infection to be lower in mice treated with probiotics than for mice treated with vehicle (FIG. 8).

The primary measurements of the immune response against influenza infection in mice that had "asthma" showed a tendency that Bl-04 could modulate immune response in the lungs during the influenza infection. The main immune cell constituents of the airways were quantified by microscopy, i.e. lymphocytes, macrophages and neutrophils. The number of macrophages on day 56 and the number of lymphocytes in the airways on day 54 were significantly higher for mice treated with probiotics than for mice receiving vehicle (FIGS. 9 and 10). Macrophages are key players in the maintenance of tissue homeostasis and control of infections, thus in the context of this model, the increase in macrophage numbers on day 56 would be expected to be a beneficial phenomenon (Tate et al. 2013). Similarly, lymphocytes are important for viral clearance and their increased presence would also be considered a positive effect.

Results from the quantitative measurements of viral load in the lung tissue can be seen in Table 9 below and in FIG. 8. These results indicate that flu titers (as normalized by reference to β-actin levels) are significantly lower on Day 54 in the probiotic group compared to the control group, supporting the position that probiotic treatment can reduce viral load and/or play a role in viral clearance.

TABLE 9

| Mouse # | Treatment | beta actin Cq 1 | beta actin Cq 2 | beta actin Cq average | Flu Cq 1 | Flu Cq 2 | Flu Cq average | Flu/beta actin Delta Cq | Flu/beta actin ratio (Cq) |
|---|---|---|---|---|---|---|---|---|---|
| 1.1 | H2O, day 52 | 19.83 | 19.38 | 19.60 | 24.33 | 24.17 | 24.25 | −4.65 | 6.51E+03 |
| 1.2 | H2O, day 52 | 20.30 | 20.15 | 20.23 | 26.33 | 26.19 | 26.26 | −6.04 | 2.88E+03 |
| 1.3 | H2O, day 52 | 20.58 | 20.20 | 20.39 | 25.74 | 25.42 | 25.58 | −5.19 | 4.73E+03 |
| 1.4 | H2O, day 52 | 19.09 | 18.76 | 18.93 | 23.48 | 23.31 | 23.40 | −4.47 | 7.24E+03 |
| 1.5 | H2O, day 52 | 20.57 | 20.01 | 20.29 | 27.52 | 26.95 | 27.23 | −6.94 | 1.69E+03 |
| 2.1 | Probiotics, day 52 | 20.02 | 19.85 | 19.94 | 25.07 | 24.82 | 24.94 | −5.01 | 5.27E+03 |
| 2.2 | Probiotics, day 52 | 19.98 | 19.39 | 19.68 | 27.02 | 26.50 | 26.76 | −7.07 | 1.56E+03 |
| 2.3 | Probiotics, day 52 | 18.84 | 18.43 | 18.64 | 23.30 | 22.96 | 23.13 | −4.49 | 7.14E+03 |
| 2.4 | Probiotics, day 52 | 20.25 | 19.85 | 20.05 | 28.76 | 27.98 | 28.37 | −8.32 | 7.51E+02 |
| 2.5 | Probiotics, day 52 | 20.53 | 20.06 | 20.30 | 25.40 | 25.24 | 25.32 | −5.02 | 5.23E+03 |
| 1.6 | H2O, day 54 | 20.20 | 19.65 | 19.93 | 23.68 | 23.19 | 23.44 | −3.51 | 1.27E+04 |
| 1.7 | H2O, day 54 | 20.09 | 19.96 | 20.03 | 24.62 | 24.34 | 24.48 | −4.46 | 7.29E+03 |
| 1.8 | H2O, day 54 | 20.03 | 19.55 | 19.79 | 23.23 | 22.85 | 23.04 | −3.24 | 1.48E+04 |
| 1.9 | H2O, day 54 | 19.15 | 18.90 | 19.02 | 22.42 | 22.47 | 22.45 | −3.42 | 1.34E+04 |
| 1.10 | H2O, day 54 | 18.93 | 18.75 | 18.84 | 21.39 | 21.18 | 21.28 | −2.44 | 2.38E+04 |
| 2.6 | Probiotics, day 54 | 20.49 | 20.25 | 20.37 | 24.40 | 24.26 | 24.33 | −3.96 | 9.77E+03 |
| 2.7 | Probiotics, day 54 | 19.51 | 19.04 | 19.27 | 22.74 | 22.22 | 22.48 | −3.21 | 1.52E+04 |
| 2.8 | Probiotics, day 54 | 19.84 | 19.47 | 19.66 | 23.38 | 23.09 | 23.23 | −3.57 | 1.22E+04 |
| 2.9 | Probiotics, day 54 | 19.84 | 19.60 | 19.72 | 23.69 | 23.49 | 23.59 | −3.87 | 1.03E+04 |
| 2.10 | Probiotics, day 54 | 19.84 | 19.30 | 19.47 | 23.32 | 23.14 | 23.23 | −3.76 | 1.10E+04 |
| 1.11 | H2O, day 56 | 20.33 | 20.05 | 20.19 | 24.30 | 23.99 | 24.15 | −3.95 | 9.80E+03 |
| 1.12 | H2O, day 56 | 21.26 | 21.01 | 21.13 | 26.49 | 26.21 | 26.35 | −5.22 | 4.65E+03 |
| 1.13 | H2O, day 56 | 19.80 | 19.54 | 19.67 | 24.28 | 24.15 | 24.22 | −4.54 | 6.92E+03 |
| 1.14 | H2O, day 56 | 19.34 | 19.11 | 19.22 | 26.58 | 26.51 | 26.54 | −7.32 | 1.35E+03 |
| 1.15 | H2O, day 56 | 19.94 | 19.49 | 19.71 | 24.45 | 24.13 | 24.29 | −4.57 | 6.81E+03 |
| 2.11 | Probiotics, day 56 | 18.80 | 18.37 | 18.58 | 24.23 | 23.73 | 23.98 | −5.40 | 4.19E+03 |
| 2.12 | Probiotics, day 56 | 19.72 | 19.32 | 19.52 | 24.10 | 23.71 | 23.90 | −4.38 | 7.60E+03 |
| 2.13 | Probiotics, day 56 | 19.25 | 19.04 | 19.15 | 24.53 | 24.20 | 24.37 | −5.22 | 4.66E+03 |
| 2.14 | Probiotics, day 56 | 19.08 | 18.72 | 18.90 | 24.49 | 24.11 | 24.30 | −5.40 | 4.19E+03 |
| 2.15 | Probiotics, day 56 | 18.05 | 17.67 | 17.86 | 23.68 | 23.43 | 23.55 | −5.69 | 3.53E+03 |

The human clinical study in healthy adults suggested that Bl-04 could modulate innate immune response (measured as IL-8) that may have suppressed the rhinovirus shedding in the nasal mucosa. In the HDM mouse model supportive evidence on the effect of Bl-04 on immune modulation was observed as increased numbers of macrophages and lymphocytes were detected in the BALF. These immunomodulatory changes could explain the improved well-being of mice and potentially lower viral titer in the lungs of the mice that are in line with the decreased rhinovirus titer in the humans. Thus Bl-04 seems to improve anti-viral immunity against rhinovirus in healthy adults and influenza in "asthmatic" mice. Overall, the results suggest that Bl-04 could be applied to asthmatic humans for preventing or alleviating virus induced asthma exacerbations.

Example 4—Human Clinical Studies

Exacerbations of Asthma and COPD in Adults

A protocol similar to described in this invention on experimental rhinovirus infection model in Example 1 is used to study the effect of Bl-04 supplementation on exacerbations of asthma and COPD (Del Vecchio 2015). Instead of healthy subjects asthmatics and COPD patients with mild to moderate disease are used by using standard clinical criteria.

The Effect of Bl-04 on Preventing and Alleviating Asthma Exacerbations Induced by HRV Study Product Probiotic Bl-04 or placebo is administered at dose of $2 \times 10^9$ CFU/day mixed into a drink for 28 days prior to HRV challenge and 4 days post infection.

Study Design

Randomized, double-blind, placebo controlled

Study Endpoints

Airflow obstruction of the subjects is measured using peak expiratory flow rate (PEF).

This is a person's maximum speed of expiration, as measured with a peak flow meter. Also Forced Expiratory Volume in one second of the predicted (FEV1% predicted) is measured or any other airflow measures needed. PEF and FEV1% predicted are measured at days −28, 0, 1, 2, and at the end of the study on day 4.

Airway inflammation is measured using the eNO measurement as per Example 1, and also by measuring IL-8 in bronchoalveolar lavage. These measurements are taken at days −28, 0, 1, 2, and 4.

Respiratory symptoms are measured using a survey at days −28, 0, 1, 2, 3 and 4 (preferably using a questionnaire and FEV).

Viral titer in bronchoalveolar and nasal lavage is measured as per Example 1.

Inclusion Criteria

Mild or moderate asthma based on PEF, FEV1% predicted and frequency of symptoms (Yawn. 2008)

18-65 years of age

Not pregnant

Exclusion Criteria

Use of anti-inflammatory drugs

Other chronic disease

Regular probiotic consumption

Antibiotic treatment

The Effect of Bl-04 on Preventing and Alleviating COPD Exacerbations Induced by HRV An identical study as per the asthma study described above is carried out, but in this case, rather than asthma the subjects have mild or moderate COPD Vestbo. 2013)

Development of Childhood Asthma

The Effect of Bl-04 on Preventing Childhood Asthma

Pregnant mothers who have a tendency for atopy (that is, allergic hypersensitivity which is known to be associated with an increase in the likelihood of developing asthma (Elward et al. 2010) and their babes are recruited into study. The probiotic Bl-04 is administered to babies from birth up to 12 years of age. The incidence of viral infections during the first year of life is monitored by visits to pediatricians and the etiology is discovered by standard laboratory techniques. In addition the development of the immune system and incidence atopy, wheezing and asthma is monitored up to 3 yrs of age by analyzing the Th2 cytokines, IgE, and using PEF, FEV1%, skin prick tests, and potentially other diagnostic measures for atopy and asthma.

Study Product

Probiotic Bl-04 or placebo is administered at dose of $2\times10^9$ CFU/day mixed into a milk starting from birth and up to 12 months of age.

Study Design

Randomized, double-blind, placebo controlled

Study Endpoints

In addition to Airflow obstruction measured as described above, the following measurements are made:—

Skin prick tests (measurement of skin reaction to allergens)

Respiratory symptoms are recorded by the parents using a questionnaire

The incidence of HRV and RSV infections are measured by parental and physician survey.

Inclusion Criteria

Atopic tendency of parents

Healthy newborns

Exclusion Criteria

Antibiotic treatment

Other congenital anomalies at birth

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in microbiology, biochemistry and molecular biology or related fields are intended to be within the scope of the following claims.

REFERENCES

Azad M B, Coneys J G, Kozyrskyj A L, Field C J, Ramsey C D, Becker A B, Friesen C, Abou-Setta A M, Zarychanski R. Probiotic supplementation during pregnancy or infancy for the prevention of asthma and wheeze: systematic review and meta-analysis. BMJ. 2013 Dec. 4; 347:f6471. doi: 10.1136/bmj.f6471.

Barrangou R., Briczinski E P, Traeger L L, Loquasto J R, Richards M, Horvath P, Coñté-Monvoisin A C, Leyer G, Rendulic S, Steele J L, Broadbent J R, Oberg T, Dudley E G, Schuster S, Romero D A, Roberts R F. Comparison of the complete genome sequences of Bifidobacterium animalis subsp. lactis DSM 10140 and Bl-04J. Bacteriol. 2009 191:4144-4151

Bartlett N W, Walton R P, Edwards M R, Aniscenko J, Caramori G, Zhu J, Glanville N, Choy K J, Jourdan P, Burnet J, Tuthill T J, Pedrick M S, Hurle M J, Plumpton C, Sharp N A, Bussell J N, Swallow D M, Schwarze J, Guy B, Almond J W, Jeffery P K, Lloyd C M, Papi A, Killington R A, Rowlands D J, Blair E D, Clarke N J, Johnston S L. Mouse models of rhinovirus-induced disease and exacerbation of allergic airway inflammation. Nat Med. 2008 February; 14(2):199-204. doi: 10.1038/nm1713. Epub 2008 Feb. 3

Calder, P C 2013. Feeding the immune system. Proc Nutr Soc 72(3): 299-309.

Cheung D, Dick E C, Timmers M C, de Klerk E P, Spaan W J, Sterk P J. Rhinovirus inhalation causes long-lasting excessive airway narrowing in response to methacholine in asthmatic subjects in vivo. Am J Respir Crit Care Med. 1995 November; 152(5 Pt 1):1490-6.

Contoli M, Message S D, Laza-Stanca V, Edwards M R, Wark P A, Bartlett N W, Kebadze T, Mallia P, Stanciu L A, Parker H L, Slater L, Lewis-Antes A, Kon O M, Holgate S T, Davies D E, Kotenko S V, Papi A, Johnston S L. Role of deficient type III interferon-lambda production in asthma exacerbations. Nat Med. 2006 September; 12(9):1023-6. Epub 2006 Aug. 13.

Contoli M, Caramori G, Mallia P, Papi A, Johnston S L. A human rhinovirus model of chronic obstructive pulmonary disease exacerbations. Contrib Microbiol. 2007; 14:101-12. Review.

Del Vecchio A M, Branigan P J, Barnathan E S, Flavin S K, Silkoff P E, Turner R B. (2015) Utility of animal and in vivo experimental infection of humans with rhinoviruses in the development of therapeutic agents for viral exacerbations of asthma and chronic obstructive pulmonary disease. Pulm Pharmacol Ther. 2014 Nov. 13; 30C:32-43. doi: 10.1016/j.pupt.2014.10.005. [Epub ahead of print] PMID:25445932[PubMed—as supplied by publisher]

Elazab N, Mendy A, Gasana J, Vieira E R, Quizon A, Forno E. Probiotic administration in early life, atopy, and asthma: a meta-analysis of clinical trials. Pediatrics. 2013 September; 132(3):e666-76. doi: 10.1542/peds.2013-0246. Epub 2013 Aug. 19.

Elward, Graham Douglas, Kurtis S. (2010). Asthma. London: Manson Pub. pp. 27-29. ISBN 978-1-84076-513-7.

FAO/WHO. Guidelines for the evaluation of probiotics in food 2001. Food and Agriculture Organization of the United Nations (FAO). 2001. Health and Nutritional Properties of Probiotics in Food including Powder Milk with Live Lactic Acid Bacteria, http://www.who.int/food-safety/publications/fs_manaqement/en/probiotics.pdf Gunawardana N, Finney L, Johnston S L, Mallia P. Experimental rhinovirus infection in COPD: implications for antiviral therapies. Antiviral Res. 2014 February; 102:95-105. doi: 10.1016/j.antiviral.2013.12.006. Epub 2013 Dec. 24. Review.

Hao Q, Lu Z, Dong B R, Huang C Q, Wu T. Probiotics for preventing acute upper respiratory tract infections. Cochrane Database Syst Rev. 2011 Sep. 7; (9):CD006895. doi: 10.1002/14651858.CD006895.pub2. Review.

Heikkinen T, Järvinen A. The Common Cold. Lancet. 2003 Jan. 4; 361(9351):51-9. Review.

Jackson D J, Evans M D, Gangnon R E, Tisler C J, Pappas T E, Lee W M, Gern J E, Lemanske R F Jr. Evidence for a causal relationship between allergic sensitization and rhinovirus wheezing in early life. Am J Respir Crit Care Med. 2012 Feb. 1; 185(3):281-5. doi: 10.1164/rccm.201104-06600C. Epub 2011 Sep. 29.

Kang E J, Kim S Y, Hwang I H, Ji Y J. The effect of probiotics on prevention of common cold: a meta-analysis of randomized controlled trial studies. Korean J Fam Med. 2013 January; 34(1):2-10. doi: 10.4082/kjfm.2013.34.1.2. Epub 2013 Jan. 28.

Mallia P, Message S D, Contoli M, Gray K K, Telcian A, Laza-Stanca V, Papi A, Stanciu L A, Elkin S, Kon O M, Johnson M, Johnston S L. Neutrophil adhesion molecules in experimental rhinovirus infection in COPD. Respir Res. 2013 Jul. 8; 14:72. doi: 10.1186/1465-9921-14-72.

Maynard, C L, Elson, C O, et al. 2012. Reciprocal interactions of the intestinal microbiota and immune system. Nature 489(7415): 231-241.

Message S D, Laza-Stanca V, Mallia P, Parker H L, Zhu J, Kebadze T, Contoli M, Sanderson G, Kon O M, Papi A, Jeffery P K, Stanciu L A, Johnston S L. Rhinovirus-induced lower respiratory illness is increased in asthma and related to virus load and Th1/2 cytokine and IL-10 production. Proc Natl Acad Sci USA. 2008 Sep. 9; 105(36):13562-7. doi: 10.1073/pnas.0804181105. Epub 2008 Sep. 3.

Proud D. Role of rhinovirus infections in asthma. Asian Pac J Allergy Immunol. 2011 September; 29(3):201-8. Review.

Saglani S. Innate immunity in paediatric viral wheezers is virus specific and not interferon dependent. Thorax. 2014 October; 69(10):887-8. doi: 10.1136/thoraxjnl-2014-205561. Epub 2014 May 28. No abstract available.

Saraya T, Kurai D, Ishii H, Ito A, Sasaki Y, Niwa S, Kiyota N, Tsukagoshi H, Kozawa K, Goto H, Takizawa H. Epidemiology of virus-induced asthma exacerbations: with special reference to the role of human rhinovirus. Front Microbiol. 2014 May 26; 5:226. doi: 10.3389/fmicb.2014.00226. eCollection 2014. Review.

Schneider D, Hong J Y, Popova A P, Bowman E R, Linn M J, McLean A M, Zhao Y, Sonstein J, Bentley J K, Weinberg J B, Lukacs N W, Curtis J L, Sajjan U S, Hershenson M B. Neonatal rhinovirus infection induces mucous metaplasia and airways hyperresponsiveness. J Immunol. 2012 Mar. 15; 188(6):2894-904. doi: 10.4049/jimmunol.1101391. Epub 2012 Feb. 13

Schwarze J, Hamelmann E, Bradley K L, Takeda K, Gelfand E W. Respiratory syncytial virus infection results in airway hyperresponsiveness and enhanced airway sensitization to allergen. J Clin Invest. 1997 Jul. 1; 100(1): 226-33.

Sigurs N, Aljassim F, Kjellman B, Robinson P D, Sigurbergsson F, Bjarnason R, Gustafsson P M. Asthma and allergy patterns over 18 years after severe RSV bronchiolitis in the first year of life. Thorax. 2010 December; 65(12):1045-52. doi: 10.1136/thx.2009.121582. Epub 2010 Jun. 27.

Stevenson C S, Docx C, Webster R, Battram C, Hynx D, Giddings J, Cooper P R, Chakravarty P, Rahman I, Marwick J A, Kirkham P A, Charman C, Richardson D L, Nirmala N R, Whittaker P, Butler K. Comprehensive gene expression profiling of rat lung reveals distinct acute and chronic responses to cigarette smoke inhalation. Am J Physiol Lung Cell Mol Physiol. 2007 November; 293(5): L1183-93. Epub 2007 Aug. 24.

Stevenson C S, Birrell M A. Moving towards a new generation of animal models for asthma and COPD with improved clinical relevance. Pharmacol Ther. 2011 May; 130(2):93-105. doi: 10.1016/j.pharmthera.2010.10.008. Epub 2010 Nov. 11. Review. PMID:21074553[PubMed—indexed for MEDLINE]

Tate M D, Pickett D L, van Rooijen N, Brooks A G and Reading P C. Critical role of airway macrophages in modulating disease severity during influenza virus infection of mice. J Virol 2010, 84(15), pp. 7569-7580.

Tourneur, E and Chassin, C 2013. Neonatal immune adaptation of the gut and its role during infections. Clin Dev Immunol 2013: 270301.

Vestbo, Jørgen 2013. "Diagnosis and Assessment". Global Strategy for the Diagnosis, Management, and Prevention of Chronic Obstructive Pulmonary Disease. Global Initiative for Chronic Obstructive Lung Disease. pp. 9-17

Wall, R, Ross, R P, et al. 2009. Role of gut microbiota in early infant development. Clin Med Pediatr 3: 45-54.

Wark P A, Johnston S L, Simpson J L, Hensley M J, Gibson P G. *Chlamydia pneumoniae* immunoglobulin A reactivation and airway inflammation in acute asthma. Eur Respir J. 2002 October; 20(4):834-40.

Yawn B P. Factors accounting for asthma variability: achieving optimal symptom control for individual patients. Primary Care Respiratory Journal 2008. 17 (3): September:138-147.

The invention claimed is:

1. A method for reducing replication of a virus and/or inflammation caused by a virus infection in a subject in need thereof, wherein:
the method comprises administering to the subject a composition comprising an effective amount of *Bifidobacterium animalis* subsp. *Lactis* BL-04 or a fermentation product or cell lysate thereof, and the virus comprises a rhinovirus or an influenza virus.

2. The method according to claim 1, wherein inflammation caused by the virus infection is reduced in the subject.

3. A method for reducing a level of one or more cytokines and/or chemokines caused by a virus infection in a subject in need thereof, wherein:
the method comprises administering to the subject a composition comprising an effective amount of *Bifidobacterium animalis* subsp. *Lactis* BL-04 or a fermentation product or cell lysate thereof, and the virus comprises a rhinovirus or an influenza virus.

4. The method according to claim 3, wherein the method comprises modulation of the subject's innate immune system, adaptive immune system or both.

5. The method according to claim 3, wherein T-helper cells specific to the virus are increased in the subject.

6. The method according to claim 1, wherein the composition is formulated as a medicament, a food product or a dietary supplement.

7. The method according to claim 1, wherein said composition also comprises at least one further probiotic microorganism.

8. The method according to claim 1, wherein said composition also comprises one or more of an anti-microbial agent, a stabilising agent, a dye and a drying agent.

9. The method according to claim 1, wherein; the subject is at risk of developing a chronic respiratory disease, and the method reduces the risk.

10. The method according to claim 1, wherein the virus comprises a human rhinovirus.

11. The method according to claim 3, wherein IL-8, IL-1beta and/or MCP-1 is/are reduced in the subject.

12. The method according to claim 1, wherein the composition comprises an effective amount of *Bifidobacterium animalis* subsp. *lactis* BL-04.

13. The method according to claim 12, wherein the subject is a human.

14. The method according to claim 12, wherein IL-8 is reduced in the subject.

15. The method according to claim 12, wherein virus replication is reduced in the subject.

16. The method according to claim 12, wherein virus shedding is reduced in the subject.

17. The method according to claim 12, wherein the virus comprises an influenza virus.

18. The method according to claim 3, wherein the composition comprises an effective amount of *Bifidobacterium animalis* subsp. *lactis* BL-04.

19. The method according to claim 18, wherein a cytokine level is reduced in the subject.

20. The method according to claim 18, wherein IL-8 is reduced in the subject.

21. The method according to claim 18, wherein virus shedding is reduced in the subject.

22. A method for reducing virus shedding or an IL8 level in a virus-infected subject in need thereof, wherein: the method comprises administering to the subject a composition comprising an effective amount of *Bifidobacterium animalis* subsp. *Lactis* BL-04 or a fermentation product or cell lysate thereof, and the virus comprises a rhinovirus or an influenza virus.

23. The method according to claim 22, wherein the composition comprises an effective amount of *Bifidobacterium animalis* subsp. *lactis* BL-04.

24. The method according to claim 23, wherein IL-8 is reduced in the subject.

25. The method according to claim 23, wherein virus shedding is reduced in the subject.

26. The method according to claim 23, wherein;
the subject is at risk of developing a chronic respiratory disease, and
the method reduces the risk.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: artificial sequence
<220> FEATURE:
<223> OTHER INFORMATION: primer

<400> SEQUENCE: 1
ggactgcagc gtagacgctt         20

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
catcctgtat atgaggccca t        21

```
<210> SEQ ID NO 3
<211> LENGTH: 24
<212> TYPE: DNA
<213> ORGANISM: Artificial sequence
<220> FEATURE:
<223> OTHER INFORMATION: Beta-actin Forward primer

<400> SEQUENCE: 3
gatcaagatc attgctcctc ctga                                           24

<210> SEQ ID NO 4
<211> LENGTH: 20
<212> TYPE: DNA
<213> ORGANISM: artificial sequence
<220> FEATURE:
<223> OTHER INFORMATION: Beta-actin Reverse primer

<400> SEQUENCE: 4
cagctcagta acagtccgcc                                                20
```